(12) United States Patent
Tropper et al.

(10) Patent No.: US 8,924,249 B2
(45) Date of Patent: *Dec. 30, 2014

(54) APPARATUS FOR DETECTING AND RECORDING ACTIVITY AND ASSOCIATED METHODS

(71) Applicant: Fitbit, Inc., San Francisco, CA (US)

(72) Inventors: Seth A. Tropper, Marlboro, NJ (US); Amado Batour, Somerset, NJ (US)

(73) Assignee: Fitbit, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/165,500

(22) Filed: Jan. 27, 2014

(65) Prior Publication Data

US 2014/0142467 A1 May 22, 2014

Related U.S. Application Data

(63) Continuation of application No. 13/869,670, filed on Apr. 24, 2013, which is a continuation of application (Continued)

(51) Int. Cl.
*A61B 5/11* (2006.01)
*A61B 5/00* (2006.01)

(Continued)

(52) U.S. Cl.
CPC ............... *A61B 5/486* (2013.01); *A61B 5/1118* (2013.01); *A61B 5/1126* (2013.01); *A61B 5/14539* (2013.01); *A61B 5/681* (2013.01);

(Continued)

(58) Field of Classification Search
None
See application file for complete search history.

(56) References Cited

U.S. PATENT DOCUMENTS

| 2,284,849 A | 8/1941 | Anderson et al. |
| 2,717,736 A | 9/1955 | Schlesinger |

(Continued)

FOREIGN PATENT DOCUMENTS

| JP | 11347021 | 12/1999 |
| WO | WO 2008/038141 | 4/2008 |
| WO | WO 2009/042965 | 4/2009 |

OTHER PUBLICATIONS

Deepak et al., Plug-and-Play, Single-Chip Photoplethysmography, 34th Annual International Conference of the IEEE EMBS, San Diego, California USA, Aug. 28-Sep. 1, 2012, 4 pages.

(Continued)

*Primary Examiner* — Robert R Niquette
(74) *Attorney, Agent, or Firm* — Martine Penilla Group, LLP

(57) ABSTRACT

A band formed to secure to a part of a human body. The band including a motion detection component. The motion detection component including circuitry for detecting and recording movement of the motion detection component. The motion detection component including a display defined to provide a visual indication of an amount of movement recorded by the circuitry. The circuitry including an electrical contact for electrical communication of signals associated with the detected and recorded movement of the motion detection component.

30 Claims, 18 Drawing Sheets

Related U.S. Application Data

No. 12/239,613, filed on Sep. 26, 2008, which is a continuation-in-part of application No. 11/862,059, filed on Sep. 26, 2007, now Pat. No. 8,177,260.

(60) Provisional application No. 60/847,538, filed on Sep. 26, 2006, provisional application No. 60/975,411, filed on Sep. 26, 2007, provisional application No. 61/023,119, filed on Jan. 24, 2008.

(51) Int. Cl.

| | | |
|---|---|---|
| *A61B 5/145* | (2006.01) | |
| *G06Q 30/02* | (2012.01) | |
| *G09F 3/00* | (2006.01) | |
| *A63B 71/06* | (2006.01) | |
| *A63F 13/20* | (2014.01) | |
| *G06F 19/00* | (2011.01) | |
| *G07F 17/32* | (2006.01) | |
| *A63B 24/00* | (2006.01) | |

(52) U.S. Cl.
CPC .............. *A61B 5/6828* (2013.01); *G06Q 30/02* (2013.01); *G06Q 30/0264* (2013.01); *G09F 3/005* (2013.01); *A61B 5/0004* (2013.01); *A61B 5/6831* (2013.01); *A61B 5/6896* (2013.01); *A61B 5/6897* (2013.01); *A61B 5/6898* (2013.01); *A61B 5/7264* (2013.01); *A61B 5/743* (2013.01); *A63B 71/06* (2013.01); *A63F 13/06* (2013.01); *G06Q 30/0207* (2013.01); *G06Q 30/0217* (2013.01); *G06F 19/36* (2013.01); *G07F 17/3244* (2013.01); *A61B 2560/0456* (2013.01); *A63B 24/0059* (2013.01); *A61B 2560/0412* (2013.01); *A61B 2562/0219* (2013.01)
USPC ......... 705/14.22; 455/414.1; 482/8; 600/300; 705/3; 705/14.12

(56) References Cited

U.S. PATENT DOCUMENTS

| | | |
|---|---|---|
| 2,883,255 A | 4/1959 | Anderson |
| 3,163,856 A | 12/1964 | Kirby |
| 3,250,270 A | 5/1966 | Bloom |
| 3,918,658 A | 11/1975 | Beller |
| 4,192,000 A | 3/1980 | Lipsey |
| 4,244,020 A | 1/1981 | Ratcliff |
| 4,281,663 A | 8/1981 | Pringle |
| 4,284,849 A | 8/1981 | Anderson et al. |
| 4,312,358 A | 1/1982 | Barney |
| 4,367,752 A | 1/1983 | Jimenez et al. |
| 4,390,922 A | 6/1983 | Pelliccia |
| 4,407,295 A | 10/1983 | Steuer et al. |
| 4,425,921 A | 1/1984 | Fujisaki et al. |
| 4,575,804 A | 3/1986 | Ratcliff |
| 4,578,769 A | 3/1986 | Frederick |
| 4,617,525 A | 10/1986 | Lloyd |
| 4,887,249 A | 12/1989 | Thinesen |
| 4,977,509 A | 12/1990 | Pitchford et al. |
| 5,058,427 A | 10/1991 | Brandt |
| 5,224,059 A | 6/1993 | Nitta et al. |
| 5,295,085 A | 3/1994 | Hoffacker |
| 5,323,650 A | 6/1994 | Fullen et al. |
| 5,446,705 A | 8/1995 | Haas et al. |
| 5,456,648 A | 10/1995 | Edinburg et al. |
| 5,583,776 A | 12/1996 | Levi et al. |
| 5,671,162 A | 9/1997 | Werbin |
| 5,704,350 A | 1/1998 | Williams, III |
| 5,724,265 A | 3/1998 | Hutchings |
| 5,890,128 A | 3/1999 | Diaz et al. |
| 5,891,042 A | 4/1999 | Sham et al. |
| 5,894,454 A | 4/1999 | Kondo |
| 5,899,963 A | 5/1999 | Hutchings |
| 5,947,868 A | 9/1999 | Dugan |
| 5,955,667 A | 9/1999 | Fyfe |
| 5,976,083 A | 11/1999 | Richardson et al. |
| 6,018,705 A | 1/2000 | Gaudet et al. |
| 6,077,193 A | 6/2000 | Buhler et al. |
| 6,085,248 A | 7/2000 | Sambamurthy et al. |
| 6,129,686 A | 10/2000 | Friedman |
| 6,145,389 A | 11/2000 | Ebeling et al. |
| 6,183,425 B1 | 2/2001 | Whalen et al. |
| 6,213,872 B1 | 4/2001 | Harada et al. |
| 6,241,684 B1 | 6/2001 | Amano et al. |
| 6,287,262 B1 | 9/2001 | Amano et al. |
| 6,301,964 B1 | 10/2001 | Fyfe et al. |
| 6,302,789 B2 | 10/2001 | Harada et al. |
| 6,305,221 B1 | 10/2001 | Hutchings |
| 6,309,360 B1 | 10/2001 | Mault |
| 6,469,639 B2 | 10/2002 | Tanenhaus et al. |
| 6,478,736 B1 | 11/2002 | Mault |
| 6,513,381 B2 | 2/2003 | Fyfe et al. |
| 6,513,532 B2 | 2/2003 | Mault et al. |
| 6,527,711 B1 * | 3/2003 | Stivoric et al. ................ 600/300 |
| 6,529,827 B1 | 3/2003 | Beason et al. |
| 6,561,951 B2 | 5/2003 | Cannon et al. |
| 6,571,200 B1 | 5/2003 | Mault |
| 6,585,622 B1 * | 7/2003 | Shum et al. ...................... 482/8 |
| 6,607,493 B2 | 8/2003 | Song |
| 6,620,078 B2 | 9/2003 | Pfeffer |
| 6,678,629 B2 | 1/2004 | Tsuji |
| 6,699,188 B2 | 3/2004 | Wessel |
| 6,761,064 B2 | 7/2004 | Tsuji |
| 6,790,178 B1 | 9/2004 | Mault et al. |
| 6,808,473 B2 | 10/2004 | Hisano et al. |
| 6,811,516 B1 | 11/2004 | Dugan |
| 6,813,582 B2 | 11/2004 | Levi et al. |
| 6,813,931 B2 | 11/2004 | Yadav et al. |
| 6,856,938 B2 | 2/2005 | Kurtz |
| 6,862,575 B1 | 3/2005 | Anttila et al. |
| 7,062,225 B2 | 6/2006 | White |
| 7,162,368 B2 | 1/2007 | Levi et al. |
| 7,171,331 B2 | 1/2007 | Vock et al. |
| 7,200,517 B2 | 4/2007 | Darley et al. |
| 7,246,033 B1 | 7/2007 | Kudo |
| 7,261,690 B2 | 8/2007 | Teller et al. |
| 7,272,982 B2 | 9/2007 | Neuhauser et al. |
| 7,373,820 B1 | 5/2008 | James |
| 7,443,292 B2 | 10/2008 | Jensen et al. |
| 7,457,724 B2 | 11/2008 | Vock et al. |
| 7,467,060 B2 | 12/2008 | Kulach et al. |
| 7,505,865 B2 | 3/2009 | Ohkubo et al. |
| 7,559,877 B2 | 7/2009 | Parks et al. |
| 7,653,508 B1 | 1/2010 | Kahn et al. |
| 7,690,556 B1 | 4/2010 | Kahn et al. |
| 7,713,173 B2 | 5/2010 | Shin et al. |
| 7,762,952 B2 | 7/2010 | Lee et al. |
| 7,774,156 B2 | 8/2010 | Niva et al. |
| 7,789,802 B2 | 9/2010 | Lee et al. |
| 7,881,902 B1 | 2/2011 | Kahn et al. |
| 7,927,253 B2 | 4/2011 | Vincent et al. |
| 7,983,876 B2 | 7/2011 | Vock et al. |
| 8,028,443 B2 | 10/2011 | Case, Jr. |
| 8,055,469 B2 | 11/2011 | Kulach et al. |
| 8,099,318 B2 | 1/2012 | Moukas et al. |
| 8,177,260 B2 | 5/2012 | Tropper et al. |
| 8,180,591 B2 | 5/2012 | Yuen et al. |
| 8,180,592 B2 | 5/2012 | Yuen et al. |
| 8,311,769 B2 | 11/2012 | Yuen et al. |
| 8,311,770 B2 | 11/2012 | Yuen et al. |
| 8,386,008 B2 | 2/2013 | Yuen et al. |
| 8,437,980 B2 | 5/2013 | Yuen et al. |
| 8,463,576 B2 | 6/2013 | Yuen et al. |
| 8,463,577 B2 | 6/2013 | Yuen et al. |
| 8,543,185 B2 | 9/2013 | Yuen et al. |
| 8,543,351 B2 | 9/2013 | Yuen et al. |
| 8,548,770 B2 | 10/2013 | Yuen et al. |
| 8,583,402 B2 | 11/2013 | Yuen et al. |
| 8,597,093 B2 | 12/2013 | Engelberg et al. |
| 8,670,953 B2 | 3/2014 | Yuen et al. |
| 2001/0055242 A1 | 12/2001 | Deshmukh et al. |

(56) References Cited

U.S. PATENT DOCUMENTS

| | | |
|---|---|---|
| 2002/0013717 A1 | 1/2002 | Ando et al. |
| 2002/0077219 A1* | 6/2002 | Cohen et al. .................. 482/8 |
| 2002/0082144 A1 | 6/2002 | Pfeffer |
| 2002/0109600 A1 | 8/2002 | Mault et al. |
| 2002/0178060 A1 | 11/2002 | Sheehan |
| 2002/0198776 A1 | 12/2002 | Nara et al. |
| 2003/0018523 A1* | 1/2003 | Rappaport et al. .............. 705/14 |
| 2003/0050537 A1 | 3/2003 | Wessel |
| 2003/0065561 A1 | 4/2003 | Brown et al. |
| 2003/0131059 A1 | 7/2003 | Brown et al. |
| 2004/0054497 A1 | 3/2004 | Kurtz |
| 2004/0061324 A1 | 4/2004 | Howard |
| 2004/0117963 A1 | 6/2004 | Schneider |
| 2004/0152957 A1 | 8/2004 | Stivoric et al. |
| 2005/0037844 A1 | 2/2005 | Shum et al. |
| 2005/0038679 A1 | 2/2005 | Short |
| 2005/0054938 A1 | 3/2005 | Wehman et al. |
| 2005/0102172 A1 | 5/2005 | Sirmans, Jr. |
| 2005/0107723 A1 | 5/2005 | Wehman et al. |
| 2005/0228244 A1 | 10/2005 | Banet |
| 2005/0228692 A1 | 10/2005 | Hodgdon |
| 2005/0234742 A1 | 10/2005 | Hodgdon |
| 2005/0248718 A1 | 11/2005 | Howell et al. |
| 2005/0272564 A1 | 12/2005 | Pyles et al. |
| 2006/0020177 A1 | 1/2006 | Seo et al. |
| 2006/0025282 A1 | 2/2006 | Redmann |
| 2006/0047208 A1 | 3/2006 | Yoon |
| 2006/0047447 A1 | 3/2006 | Brady et al. |
| 2006/0089542 A1 | 4/2006 | Sands |
| 2006/0111944 A1* | 5/2006 | Sirmans et al. .................. 705/3 |
| 2006/0129436 A1 | 6/2006 | Short |
| 2006/0143645 A1 | 6/2006 | Vock et al. |
| 2006/0277474 A1 | 12/2006 | Robarts et al. |
| 2006/0282021 A1 | 12/2006 | DeVaul et al. |
| 2006/0287883 A1 | 12/2006 | Turgiss et al. |
| 2007/0050715 A1 | 3/2007 | Behar |
| 2007/0051369 A1 | 3/2007 | Choi et al. |
| 2007/0071643 A1 | 3/2007 | Hall et al. |
| 2007/0123391 A1 | 5/2007 | Shin et al. |
| 2007/0136093 A1 | 6/2007 | Rankin et al. |
| 2007/0155277 A1 | 7/2007 | Amitai et al. |
| 2007/0159926 A1 | 7/2007 | Prstojevich et al. |
| 2007/0179356 A1* | 8/2007 | Wessel .......................... 600/300 |
| 2007/0194066 A1 | 8/2007 | Ishihara et al. |
| 2007/0197920 A1 | 8/2007 | Adams |
| 2007/0208544 A1 | 9/2007 | Kulach et al. |
| 2007/0276271 A1 | 11/2007 | Chan |
| 2008/0093838 A1 | 4/2008 | Tropper et al. |
| 2008/0125288 A1 | 5/2008 | Case |
| 2008/0140163 A1 | 6/2008 | Keacher et al. |
| 2008/0140338 A1 | 6/2008 | No et al. |
| 2009/0018797 A1 | 1/2009 | Kasama et al. |
| 2009/0043531 A1 | 2/2009 | Kahn et al. |
| 2009/0048044 A1 | 2/2009 | Oleson et al. |
| 2009/0054737 A1 | 2/2009 | Magar et al. |
| 2009/0063193 A1 | 3/2009 | Barton et al. |
| 2009/0171788 A1 | 7/2009 | Tropper et al. |
| 2009/0271147 A1 | 10/2009 | Sugai |
| 2010/0205541 A1 | 8/2010 | Rapaport et al. |
| 2010/0217099 A1 | 8/2010 | LeBoeuf et al. |
| 2011/0003665 A1 | 1/2011 | Burton et al. |
| 2011/0009051 A1 | 1/2011 | Khedouri et al. |
| 2011/0022349 A1 | 1/2011 | Stirling et al. |
| 2011/0080349 A1 | 4/2011 | Holbein et al. |
| 2011/0106449 A1 | 5/2011 | Chowdhary et al. |
| 2011/0131005 A1 | 6/2011 | Ueshima et al. |
| 2011/0193704 A1 | 8/2011 | Harper et al. |
| 2011/0224508 A1 | 9/2011 | Moon |
| 2011/0230729 A1 | 9/2011 | Shirasaki et al. |
| 2012/0072165 A1 | 3/2012 | Jallon |
| 2012/0083705 A1 | 4/2012 | Yuen et al. |
| 2012/0083714 A1 | 4/2012 | Yuen et al. |
| 2012/0083715 A1 | 4/2012 | Yuen et al. |
| 2012/0083716 A1 | 4/2012 | Yuen et al. |
| 2012/0084053 A1 | 4/2012 | Yuen et al. |
| 2012/0084054 A1 | 4/2012 | Yuen et al. |
| 2012/0092157 A1 | 4/2012 | Tran |
| 2012/0183939 A1 | 7/2012 | Aragones et al. |
| 2012/0226471 A1 | 9/2012 | Yuen et al. |
| 2012/0226472 A1 | 9/2012 | Yuen et al. |
| 2012/0227737 A1 | 9/2012 | Mastrototaro et al. |
| 2012/0265480 A1 | 10/2012 | Oshima |
| 2012/0330109 A1 | 12/2012 | Tran |
| 2013/0006718 A1 | 1/2013 | Nielsen et al. |
| 2013/0072169 A1* | 3/2013 | Ross et al. ................. 455/414.1 |
| 2013/0073254 A1 | 3/2013 | Yuen et al. |
| 2013/0073255 A1 | 3/2013 | Yuen et al. |
| 2013/0080113 A1 | 3/2013 | Yuen et al. |
| 2013/0095459 A1 | 4/2013 | Tran |
| 2013/0096843 A1 | 4/2013 | Yuen et al. |
| 2013/0151196 A1 | 6/2013 | Yuen et al. |
| 2013/0158369 A1 | 6/2013 | Yuen et al. |
| 2013/0231574 A1 | 9/2013 | Tran |
| 2013/0261475 A1 | 10/2013 | Mochizuki |
| 2013/0267249 A1 | 10/2013 | Rosenberg |
| 2013/0268199 A1 | 10/2013 | Nielsen et al. |
| 2013/0268236 A1 | 10/2013 | Yuen et al. |
| 2013/0296666 A1 | 11/2013 | Kumar et al. |
| 2013/0296673 A1 | 11/2013 | Thaveeprungsriporn et al. |
| 2013/0310896 A1 | 11/2013 | Mass |
| 2013/0325396 A1 | 12/2013 | Yuen et al. |
| 2014/0035761 A1 | 2/2014 | Burton et al. |
| 2014/0039804 A1 | 2/2014 | Park et al. |
| 2014/0039840 A1 | 2/2014 | Yuen et al. |
| 2014/0077673 A1 | 3/2014 | Garg et al. |

OTHER PUBLICATIONS

"Automatic classification of ambulatory movements and evaluation of energy consumptions utilizing accelerometers and barometer", Ohtaki, et al, Microsystem Technologies, vol. 11, No. 8-10, Aug. 2005, pp. 1034-1040.

"Classification of Human Moving Patterns Using Air Pressure and Acceleration", Sagawa, et al, Proceedings of the 24th Annual Conference of the IEEE Industrial Electronics Society, vol. 2, Aug.-Sep. 1998, pp. 1214-1219.

"Non-restricted measurement of walking distance", Sagawa, et al, IEEE Int'l Conf. on Systems, Man, and Cybernetics, vol. 3, Oct. 2000, pp. 1847-1852.

"Activity Classification Using Realistic Data From Wearable Sensors", Parkka, et al, IEEE Transactions on Information Technology in Biomedicine, vol. 10, No. 1, Jan. 2006, pp. 119-128.

"Indoor Navigation with MEMS Sensors", Lammel, et al., Proceedings of the Eurosensors XIII conference, vol. 1, No. 1, Sep. 2009, pp. 532-535.

"Design of a Wireless Assisted Pedestrian Dead Reckoning System—The NavMote Experience", Fang, et al, IEEE Transactions on Instrumentation and Measurement, vol. 54, No. 6, Dec. 2005, pp. 2342-2358.

"On Foot Navigation: When GPS alone is not Enough", Ladetto, et al, Journal of Navigation, vol. 53, No. 2, Sep. 2000, pp. 279-285.

"A Hybrid Discriminative/Generative Approach for Modeling Human Activities", Lester, et al., Proc. of the Int'l Joint Conf. Artificial Intelligence, 2005, pp. 766-772.

"Using MS5534 for altimeters and barometers", Intersema App., Note AN501, Jan. 2006.

"Validated caloric expenditure estimation using a single body-worn sensor", Lester, et al, Proc. of the Int'l Conf. on Ubiquitous Computing, 2009, pp. 225-234.

"Drift-free dynamic height sensor using MEMS IMU aided by MEMS pressure sensor", Tanigawa, et al, Workshop on Positioning, Navigation and Communication, Mar. 2008, pp. 191-196.

"Improvement of Walking Speed Prediction by Accelerometry and Altimetry, Validated by Satellite Positioning", Perrin, et al, Medical & Biological Engineering & Computing, vol. 38, 2000, pp. 164-168.

"An Intelligent Multi-Sensor system for Pedestrian Navigation", Retscher, Journal of Global Positioning Systems, vol. 5, No. 1, 2006, pp. 110-118.

"Evaluation of a New Method of Heading Estimation of Pedestrian Dead Reckoning Using Shoe Mounted Sensors", Stirling et al., Journal of Navigation, vol. 58, 2005, pp. 31-45.

(56) References Cited

OTHER PUBLICATIONS

"Direct Measurement of Human Movement by Accelerometry", Godfrey, et al., Medical Engineering & Physics, vol. 30, 2008, pp. 1364-1386.

"Foot Mounted Inertia System for Pedestrian Naviation", Godha et al., Measurement Science and Technology, vol. 19, No. 7, May 2008, pp. 1-9.

"Altimeter and Barometer System", Clifford, et al., Freescale Semiconductor Aplication Note AN1979, Rev. 3, Nov. 2006.

"SCP 1000-D01/D11 Pressure Sensor as Barometer and Altimeter", VTI Technologies Application, Jun. 2006, Note 33.

"Suunto LUMI User Guide", Jun. and Sep. 1997.

International Search Report issued on Aug. 15, 2008, in related application PCT/IB07/03617.

\* cited by examiner

APPARATUS FOR DETECTING AND RECORDING ACTIVITY AND ASSOCIATED METHODS

CLAIM OF PRIORITY

This application is a continuation application under 35 U.S.C. 120 of prior U.S. application Ser. No. 13/869,670, filed Apr. 24, 2013, which is a continuation application under 35 U.S.C. 120 of prior U.S. application Ser. No. 12/239,613, filed on Sep. 26, 2008, which:

1) is a continuation-in-part under 35 U.S.C. 120 of prior U.S. application Ser. No. 11/862,059, filed Sep. 26, 2007, issued as U.S. Pat. No. 8,177,260, on May 15, 2012, which claims priority under 35 U.S.C. 119(e) to U.S. Provisional Patent Application No. 60/847,538, filed Sep. 26, 2006;
2) is a continuation-in-part under 35 U.S.C. 120 of PCT Application No. PCT/IB2007/003617, filed Sep. 26, 2007, which claims priority to U.S. Provisional Patent Application No. 60/847,538, filed Sep. 26, 2006;
3) claims priority under 35 U.S.C. 119(e) to U.S. Provisional Patent Application No. 60/975,411, filed Sep. 26, 2007; and
4) claims priority under 35 U.S.C. 119(e) to U.S. Provisional Patent Application No. 61/023,119, filed Jan. 24, 2008.

The disclosure of each above-identified patent application is incorporated in its entirety herein by reference.

BACKGROUND OF THE INVENTION

The present application is directed to a system and method for encouraging physical activity and in particular a system and method for utilizing a coupon to indicate the achievement or completion of physical activity for a predetermined amount and/or predetermined period of time.

Obesity has taken a front seat in public discussions and media coverage. As a nation, we have been getting steadily heavier. The number of adults who are obese has increased dramatically. An estimated 300,000 deaths each year in the United States are attributed to obesity. The economic cost of obesity in the United States was approximately $117 billion in year 2000. Obesity has reached epidemic proportions in the United States, as well as worldwide. According to national data analyzed in 2002, it is estimated that 65% of Americans are now overweight or obese, and more than 61 million adults are obese.

Adults are not the only ones who have been getting heavier. The percentage of overweight children in the United States is growing at an alarming rate, specifically, it has more than doubled since the 1970s. Children are spending less time exercising and more time in front of the television, computer, or video-game consoles. According to the Center for Disease Control, 16% (or ~9 million) of American children are substantially overweight and the number is expected to grow by 20% over the next 5 years. Some states have childhood obesity rates as high as 25%. Children who lack exercise and proper nutrients in their diet are subject to an increased risk of potential serious health related problems including stunted growth, cognitive impairment, heart disease, diabetes and a range of other illnesses.

The United States Department of Health and Human Services recommends that children and teens be physically active for at least 60 minutes on most, if not all, days. It is recommended that adults engage in at least 30 minutes of moderate-intensity physical activity, above usual activity, on most days of the week. More than 60% of adults do not achieve the recommended amount of regular physical activity. In fact, 25% of the adults in the United States do not participate in any leisure time physical activity. Physical activity declines dramatically with age during adolescence. As such, nearly 50% of young people aged 12-21 are not active on a regular basis. Physical activity is important in preventing and treating obesity and is extremely helpful in maintaining weight loss, especially when combined with a healthy diet.

Exercise is one component of the equation to solve the problem of obesity. The real challenge is motivating individuals to participate in an exercise regimen or physical activity. People's behavior must change and they must lead a lifestyle of physical activity. Corporations have become sensitive to the perception that they are socially responsible. As such, corporations strategically advertise and promote their contributions towards a healthy community and encourage physical activity. Numerous fast food restaurants have dramatically altered their menus to incorporate healthy foods thereby promoting the importance of healthy lifestyles and physical fitness.

Exercise, while rewarding in numerous ways, offers little incentive or motivation for individuals to continue to exercise and stay physically fit. Most corporations today rely on monetary coupons or rebates to encourage the purchase of a particular product or service. In the year 2000 over 330 billion coupons were distributed with approximately 4.5 redeemed for a total consumer savings of $3.6 billion. Overall, 77.3% of people use coupons.

Issuance of rewards or incentives to encourage, motivate, or promote additional physical activity or exercise is nothing new. For instance, U.S. Pat. No. 6,585,622 as well as U.S. Published Application Nos. 2005/0102172; 2003/0065561; 2002/0077219 all disclose systems in which rewards are earned based on user participation in physical activity or exercise. Rewards or points are accumulated and may be redeemed at a later point in time. Such systems require the establishment of an infrastructure so that the physical activity of the user may be monitored and the rewards of incentive points issued. In part due to the expense associated with employing such an infrastructure, these systems and methods are best suited for monitoring participation in physical activity or exercise over an extended period of time. Irrespective of the accumulation and tabulation of intangible rewards or points as they are earned over a period of time, such a protracted process is better suited for adults rather than children or teenagers who have a shorter attention span which requires more immediate gratification in today's fast paced society.

It is therefore desirable to develop a new interactive physical coupon, whereby after engaging in physical activity for a predetermined amount and/or predetermined period of time the coupon is activated and immediately redeemable providing the user with immediate satisfaction.

SUMMARY OF THE INVENTION

The present application is directed to an interactive coupon redeemable by the holder after having participated in physical activity for a predetermined period of time.

The application relates to a kinetic coupon for encouraging participation in physical activity. Initially, the kinetic coupon may be inactive when dispensed to the user. While in possession of the kinetic coupon the user participates in physical activity that is monitored by circuitry in the coupon. The circuitry determines when the user's participation in physical activity exceeds a predetermined threshold, e.g., a predetermined amount and/or predetermined period of time, After participating in physical activity that exceeds the predetermined threshold, the kinetic coupon is validated and signified to the user that it is now redeemable.

The application comprises a coupon that detects physical activity of a user using a motion detector. The motion detector may use any one of a variety of technologies such as chemical motion detectors, mechanical motion detectors, or electrical motion detectors.

A chemical motion detector according to the present application may comprise one or more chemicals which, when mixed, indicate to a user that the threshold of activity has been reached. The chemicals may be included in various reservoirs or indicator wells which mix upon physical activity and movement of the motion detector. The chemicals may also be mixed using micropumps which are powered by movement of the motion detector and dispense the chemicals from one or more reservoirs. In a further embodiment, a piezoelectric device powered by physical activity may be used to power the micropumps. The micropumps may be configured to function only upon a certain level of physical activity such that minor movements of the motion detector do not drive the micropumps.

In another embodiment, a chemical motion detector according to the present application may comprise one or more chemical solutions that react to the sweat, pH level of, biological cues, or chemicals released by or through a user's skin during and after physical activity.

In another embodiment, a chemical motion detector according to the present application may comprise one or more chemicals that are microencapsulated in small spheres that burst upon physical activity. An abrasive agent may be provided adjacent to the spheres to assist in the rupture of the spheres.

A mechanical motion detector according to the present application may comprise a number of different configurations. In one embodiment, the motion detector comprises a pendulum which moves upon physical activity of the user and causes the rotation of a ratchet gear. Once the ratchet gear has been moved a sufficient number of times, the user is presented with the indicator. Another embodiment of a mechanical motion detector to be used with the present application is a magnetic switch in which a metal ball is held in place using magnetic attraction. Physical activity of the user will force the metal ball to move and short against a contact, which is detected and used to determine when the threshold of physical activity has been reached.

Another embodiment of a mechanical motion detector comprises a conductive tube in which a conductive object such as a metal ball is disposed. A spring inside the conductive tube maintains the ball apart from a contact at the end of the tube. Motion such as physical activity of the user causes the ball to compress the spring and short against the contact at the end of the tube, which is registered by a circuit which determines when the predetermined threshold of activity has been reached.

In a further embodiment of a mechanical motion detector which may be used with the present application, a conductive element such as a ball is disposed in a bounded area on a conductive plate and surrounded by a conductive wall or conductive posts. The wall or posts are separated from the conductive plate such that the ball will close a circuit between the wall or posts and the plate when the ball touches the wall or posts. Upon physical activity of the user, the ball moves inside the bounded area and closes a circuit between the wall or posts and the plate whenever it touches them both. The bounded area may be flat and elongated in a certain direction to detect only one range of motion. The bounded area may also be a sphere in order to detect motion in every direction. The different posts may register different signals with the circuitry so that the present application may detect a predetermined threshold of various different types of physical activities which cause different motions of the motion detector. In some embodiments, a dampening device surrounds the ball in order to eliminate the detection of minor movements that do not constitute physical activity which the present application seeks to detect.

Another embodiment of a mechanical motion detector comprises a conductive pin, wire, or ribbon which may have a conductive weight on the free end. Spaced from the weight in various different directions are contact points which close a circuit upon contact with the weight. While the motion detector is not moving, the weight is not contacting any other surface, but physical activity will cause the weight to move and contact one or more contact points disposed a predetermined distance from the weight.

The coupon according to the present application has an indicator which indicates to the user when a certain threshold of physical activity has been reached. The indicator may be a change in color of the coupon, the appearance of an image or message on the coupon, a visual indicator such as a light emitting diode, or a sonic indicator.

Once the predetermined threshold of physical activity has been detected by the coupon, the coupon may be redeemed. In one embodiment, the coupon may be redeemed by bringing the coupon to a location such as a retail store or restaurant which accepts the coupon in exchange for free or discounted goods and/or services. In another embodiment, the coupon may be redeemed on an interactive web site by, for example, entering a unique code from the coupon into the web site. The unique code may be electronically revealed on a display such as, for example, a liquid crystal display or a series of light emitting diodes. The unique code may also be permanently printed on the coupon or printed on the coupon in a way that reveals all or a portion of the unique code once the predetermined threshold of physical activity has been reached. The coupon may be redeemed for users to earn free or discounted goods and/or services. In a further embodiment, the coupon may be redeemed for points or virtual currency which may be used for online goods, services, or games.

In one embodiment, the coupon is a single-use product that may be discarded upon redemption. In another embodiment, once the coupon has reached the predetermined threshold of physical activity and redeemed, it may be reset so that it may be used again. In this embodiment, the vendor who issued and collected the coupon may reset the coupon for repeated distribution. In one embodiment, the vendor may be a computer system that automatically resets the coupon without any user interaction. In another embodiment, a single user may retain the coupon and redeem the coupon for rewards each time the predetermined threshold of physical activity has been reached.

An embodiment covers a redeemable coupon comprising a housing, a motion detector coupled to the housing, wherein the motion detector detects an amount of motion of the coupon, and an indicator coupled to the motion detector, wherein the indicator is activated by the motion detector upon detecting the amount of motion.

In an embodiment the coupon may be redeemed, for example, via an electronic network. The electronic network may be, for example, the Internet or a wireless communication network. The coupon may be redeemable for items, such as, for example, money, points, prizes or an item relating to an electronic game, such as, for example. at least one of an avatar, life, strength, a weapon, a potion, money, health, ammunition, special power, food, an accessory, a pet, an article of clothing, a clue, and a key.

In an embodiment, the motion may be monitored, for example, during a predetermined time interval, or from a first predetermined point in time until a second predetermined point in time. Additionally, the at least one of the first predetermined point in time and the second predetermined point in time may be a preset date. Alternatively, at least one of the first predetermined point in time may be an activation of the motion detector and/or the second predetermined point in time may be determined from the first predetermined point in time and a predetermined time interval.

In an embodiment the redeemable coupon may further comprise computer programmable code including instructions that implement an electronic game.

In an embodiment the information indicated by the indicator may correspond to at least one of a point and a reward based on a level of motion detected by the motion detector.

In an embodiment a user may interact with an online game using the redeemable coupon. In another embodiment the indicator may present a code. In yet another embodiment the redeemable coupon may be used to interact with an online game by entering the code from the indicator. In one or more of the prior embodiments, the user may be rewarded upon detection of a predetermined level of motion by the motion detector. The reward may be at least one of money, a prize, an game item and points. The game item may be at least one of an avatar, life, strength, a weapon, a potion, money, health, ammunition, special power, food, an accessory, a pet, an article of clothing, a clue, and a key.

In an embodiment a user may be rewarded based on a level of motion detected by the motion detector. In another embodiment the user may be rewarded based on an amount of motion detected by the motion sensor.

In an embodiment the redeemable coupon may be provided together with a product offered to consumers. The redeemable coupon may comprises a packaging for the product or a label for the product.

In an embodiment the motion detector may be decoupled from the housing. In one or more of the prior embodiments the housing may be a wearable object. The wearable object may be selected from the group including a bracelet, anklet, necklace, headband, hat, scarf, glove, clothing, footwear, pin, clip, eyewear, belt and neckwear.

In an embodiment a memory may be coupled to the motion detector, wherein the memory stores information from the motion detector. The information may include the amount of motion detected.

One or more of the previous embodiments may further comprise an electronic device, wherein at least one of the motion detector is decoupled from the housing and coupled to the electronic device. The motion detector may activate at least one feature of the electronic device based on the amount of motion detected prior to decoupling. The electronic device may be at least one of a game, toy, game controller, computer interface device, cell phone, mobile data communication device, microprocessor or computer. The motion detector may be coupled to an electronic game controller. In an embodiment the coupon may further comprise an electronic device, wherein the memory is decoupled from the motion detector and coupled to the electronic device. The electronic device may be at least one of a game, toy, game controller, computer interface device, cell phone, mobile data communication device, microprocessor or computer. In one or more of the prior embodiments the electronic device may be usable for a period of time corresponding to the amount of motion detected. In one embodiment the coupon may further comprise a base station, wherein at least one of the motion detector and the memory is coupled to the base station. The base station may be in communication with a processing arrangement. The processing arrangement may control an interactive game.

In one embodiment at least one of the motion detector and the memory may enable a feature of the electronic device.

In an embodiment the coupon may further comprise a transmitter, wherein the transmitter may be used to communicate with a wireless network. In an embodiment the coupon may further comprise an electronic device, wherein the memory communicates with the electronic device using the transmitter.

In one or more of the embodiments the motion detector may distinguish between levels of physical activity. Alternatively or additionally, the motion detector may distinguish between types of physical activity. The indicator may comprise a plurality of indicators. Each of the plurality of indicators may correspond to a type of physical activity.

In an embodiment the indicator may be a code which may be used for redeeming the coupon from a remote location. The coupon may be redeemed via a web site. The coupon may be redeemed via a portable electronic device.

In an embodiment the motion detector may activate a plurality of indicators upon the attainment of a plurality of predetermined limits. The motion detector may be adapted to deactivate the indicator when a predetermined threshold of inactivity is reached.

In one or more of the above embodiments the coupon may be coupled to a bracelet. The coupon may be formed of flexible material. In one or more of the above embodiments at least one of the motion detector and indicator may be reset or resettable.

An embodiment covers a method of providing an incentive for a user to exercise comprising providing the user with a coupon to be coupled to the user, monitoring the motion of the user with a motion sensor included in the coupon, and activating the coupon when the motion sensor has detected a predetermined amount of motion such that the coupon becomes redeemable by the user. The method may further comprise indicating to the user when the motion sensor has detected a predetermined amount of motion. The method may also comprise redeeming the coupon. The coupon may be redeemed, for example, via an electronic network. The electronic network may be, for example, the Internet or a wireless communication network. In an embodiment the coupon may be redeemable for money, points, prizes or an item relating to an electronic game. In an embodiment the item may be at least one of an avatar, life, strength, a weapon, a potion, money, health, ammunition, special power, food, an accessory, a pet, an article of clothing, a clue, and a key.

In an embodiment the motion may be monitored, for example, during a predetermined time interval or from a first predetermined point in time until a second predetermined point in time. In an embodiment at least one of the first predetermined point in time and the second predetermined point in time may be a preset date. In an embodiment at least one of the first predetermined point in time may be an activation of the motion sensor. In an embodiment the second predetermined point in time may be determined from the first predetermined point in time and a predetermined time interval.

In an embodiment the coupon may comprise a game. An embodiment may further comprise issuing at least one of a point and a reward to the user based on a level of motion monitored by the motion sensor. An embodiment may further comprise the user interacting with an online game using the coupon. Another embodiment may further comprise the coupon presenting a code. An embodiment may further comprise interacting with an online game by entering the code provided by the coupon. An embodiment may further comprise rewarding the user upon detection of a predetermined level of motion by the motion sensor. The reward may be at least one of money, a prize, a game item and points. The game item may be at least one of an avatar, life, strength, a weapon, a potion, money, health, ammunition, special power, food, an accessory, a pet, an article of clothing, a clue, and a key. An embodiment may further comprise rewarding the user based on a level of motion detected by the motion sensor. An embodiment may further comprise rewarding the user based on an amount of motion detected by the motion sensor.

In an embodiment the coupon may be provided with a product offered to consumers. The coupon may comprise a packaging for the product. The coupon may comprise a label for the product.

An embodiment further comprises decoupling the motion sensor from the coupon. In an embodiment the coupon may be a wearable object. The wearable object may be selected from the group including a bracelet, anklet, necklace, headband, hat, scarf, glove, clothing, footwear, pin, clip, eyewear, belt and neckwear.

In an embodiment the motion sensor may include a memory that stores information from the motion detector. The information may include the amount of motion detected. An embodiment may further comprise coupling the motion sensor to an electronic device. An embodiment may further comprise activating at least one feature of the electronic device based on the amount of motion detected prior to decoupling. The electronic device may be at least one of a game, toy, game controller, computer interface device, cell phone, mobile data communication device, microprocessor or computer. An embodiment may further comprise coupling the motion sensor to an electronic game controller. An embodiment may further comprise coupling the memory to the electronic device. The electronic device may be at least one of a game, toy, game controller, computer interface device, cell phone, mobile data communication device, microprocessor or computer. The electronic device may be usable for a period of time corresponding to the amount of motion detected.

An embodiment may further comprise coupling at least one of the motion sensor and the memory to a base station. An embodiment may further comprise communicating between the base station and a processing arrangement. Another embodiment may further comprise controlling an interactive game from the processing arrangement. An embodiment may further comprise enabling a feature of the electronic device by at least one of the motion sensor and the memory. Another embodiment may further comprise enabling a feature of the electronic device by at least one of the motion sensor and the memory. An additional embodiment may further comprise communicating with a wireless device using a transmitter. Another embodiment may further comprise communicating between the memory and an electronic device using the transmitter.

In an embodiment the predetermined amount of motion may be based on a level of physical activity. In an embodiment the motion sensor may distinguish between types of physical activity. The predetermined amount of motion may comprise a plurality of predetermined amounts of motion. Each of the plurality of predetermined amounts of motion may correspond to a type of physical activity.

In an embodiment the coupon may be activated by providing a code which may be used for redeeming the coupon from a remote location. In an embodiment the coupon may be redeemed via a web site. In another embodiment the coupon may be redeemed via a portable electronic device.

Another embodiment further comprises activating the coupon upon the attainment of a plurality of predetermined limits. An embodiment further comprises deactivate the coupon when a predetermined threshold of inactivity is reached.

In an embodiment the coupon may be coupled to a bracelet. In an embodiment the coupon may be formed of flexible material. In an embodiment at least one of the motion detector and indicator may be reset or resettable. Another embodiment may further comprise decoupling the motion sensor from the coupon.

BRIEF DESCRIPTION OF THE DRAWINGS

The foregoing and other features of the present application of the present application will be more readily apparent from the following detailed description and drawings of illustrative embodiments of the application wherein like reference numbers refer to similar elements throughout the several views in which.

DETAILED DESCRIPTION

Figure 1:
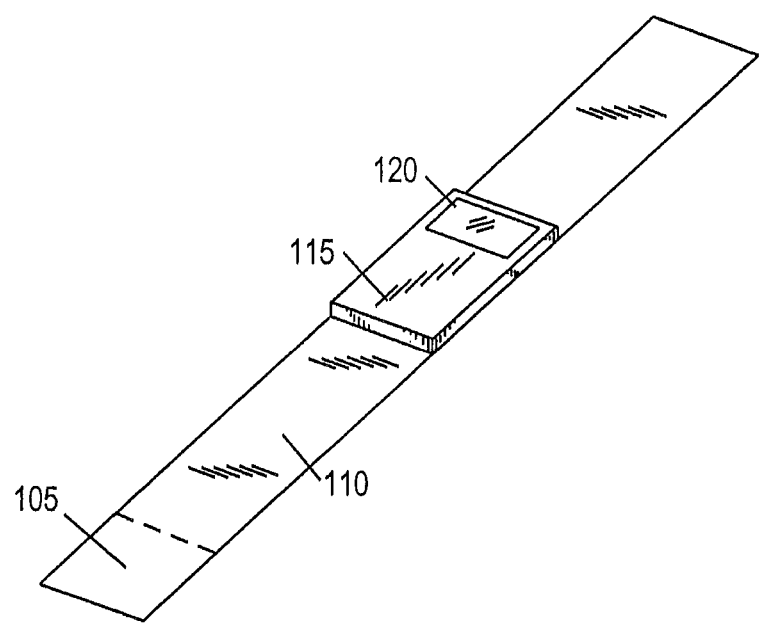
FIG. 1 is a enlarged perspective view of the exemplary kinetic coupon in accordance with the present application.

The present application is directed to an interactive or "kinetic" coupon that is a physical device which is redeemable, activated or validated only after the user has participated in movement or physical activity of a predetermined amount and/or for a predetermined period of time. Referring to FIG. 1, the kinetic coupon 100 has a housing 115 in which is enclosed components for monitoring the extent of physical activity or movement by the user and activating an indicator to signify to the user when the kinetic coupon is redeemable, activated or validated. A display 120 such as, for example, a light emitting diode (LED), liquid crystal display (LCD) or other display device is provided for display of some type of indicia indicating when the physical activity exceeds a predetermined threshold, i.e., a predetermined amount and/or predetermined period of time. The indicator may simply be a color indicator (e.g., change from colorless to a color, change of color or change from opaque to transparent to reveal some indicia otherwise not previously visible). For instance, after participating in physical activity for a predetermined period of time, a green color may be indicated on the display 120. Alternatively, written indicia may be observed in the display 120. Any desired alphanumeric word or message may be displayed. In one embodiment, the written indicia may display some sort of encouragement such as "Keep Going", "Don't Stop" before the predetermined time period has expired in which the user has participated in physical activity or movement. Once the wearer has participated in physical activity for the predetermined threshold the indicia is activated to reflect the redeemable value of the coupon and/or perhaps the location at which the coupon is to be redeemed. By way of example, upon engaging in physical activity or movement for the predetermined period of time, the display 120 may read "Free Frisbee" and the name of the participating vendor from whom the toy may be redeemed. The kinetic coupon may alternatively, or in addition to a visual indicator, include an audible alarm and associated circuitry for producing an audible alarm. Upon the engagement of physical activity that exceeds the predetermined threshold, the kinetic coupon will produce or generate an audible sound to inform the wearer that the coupon may now be redeemed. Such audible alarm may be a beep, melody, word, phrase or instructions as to how to go about redeeming the value of the coupon.

The coupon may be redeemable on an interactive web site for free or discounted goods and/or services. The coupon may, for example, display a code when the predetermined threshold has been reached. The coupon may also display a code which will only be accepted by a vendor once the coupon has issued an indicator that the threshold level of physical activity has been reached. The user may then enter the code into the web site to be redeemed. The coupon may also be redeemed for points or virtual currency in an online game or in an online gaming environment. The points or virtual currency may be used to purchase additional games. In some games, the coupon may be redeemed for rewards specific to that game such as, for example, special playable characters, special playable levels, costumes for a character, character energy or health, or playable items that that may be branded with the logo of the entity that issued the bracelet. For example, in a car racing game, the user may be able to redeem the coupon for a playable car that is branded with a vendor's logo.

In one embodiment, the coupon may communicate with a computer system which includes a computer game. The user may participate in the game by achieving a predetermined level of physical activity for an extended period of time. In one embodiment, the game comprises a virtual character such as a virtual pet whose health and progress through a game is determined by the physical activity of the user as measured by the coupon.

Figure 2:
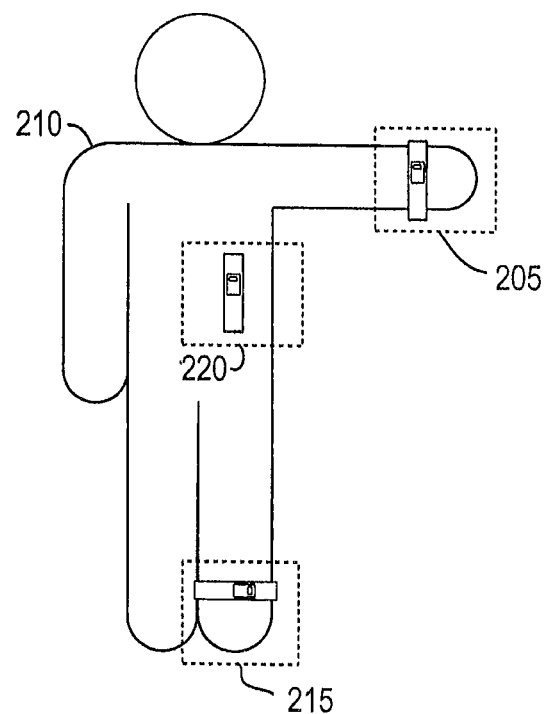
FIG. 2 is an exemplary kinetic coupon in accordance with the present application shown being worn on different parts of the body.

Kinetic coupon 100 may be secured about a part of the body, for example, by a band or strap 110. FIG. 2 shows several exemplary positions of the kinetic coupon 100 worn on the Body 210, e.g., about the wrist 205 or ankle 215. Other parts of the body 210 may be chose such as, but not limited to, the head, earlobe, neck, arm, finger, leg, toe, or waist. As shown in FIG. 1, the strap 110 may also include a securing device 105. The securing device 105 may be, but need not necessarily be, releasable such as hook-n-eye, VEL-CROTM™, a buckle, a snap or a clasp. In the case that the securing device 105 is not releasable, then the strap may be broken or torn after use and discarded either alone or with the housing 115 and components disposed therein. Yet another variation of the present application would eliminate the securing device 105 altogether whereby the strap would be made of a material such as a thin metal or plastic band that in a relaxed state is wound into a coil, but upon the application of a force may be stretched out substantially straight. After being positioned about a portion of the body the force exerted on the band is removed allowing it to return to its relaxed state and substantially conform about a part of the user's body. the strap may be custom designed and printed, as desired, for instance, to identify a corporate name and/or promotional item or an advertiser.

Alternatively, the strap 110 itself may also be eliminated and the kinetic coupon 100 releasable secured directly to the wearer's body or clothing via an adhesive strip, pin or other device. This alternative embodiment is particularly well suited for placement of the kinetic coupon on rather than about a part of the body such as depicted in FIG. 2 by coupon 220 worn on the wearer's chest. Instead of being worn on or about the user's body or clothing, the kinetic coupon may simply be held in the user's hand.

As previously mentioned the coupon 100 includes components for indicating when the user's participation in physical activity or movement exceeds a predetermined threshold, e.g., a predetermined amount and/or predetermined period of time, required to activate or validate the coupon. The kinetic coupon may be designed to require either continuous or non-continuous physical activity or movement. Functionality for monitoring the extent of the user's participation in physical activity or movement may be achieved using chemical, mechanical and electrical technology either exclusively or in combination thereof. It is advantageous to minimize the cost of manufacture and overall size when designing the components for monitoring the extent of participation in physical activity or movement by the user. An illustrative example of a system for monitoring the extent of user's participation in physical activity or movement utilizing each of the three different technologies will be described, however, alternative devices such as piezoelectric devices or pedometers are contemplated and within the intended scope of the present application.

Figure 3A:
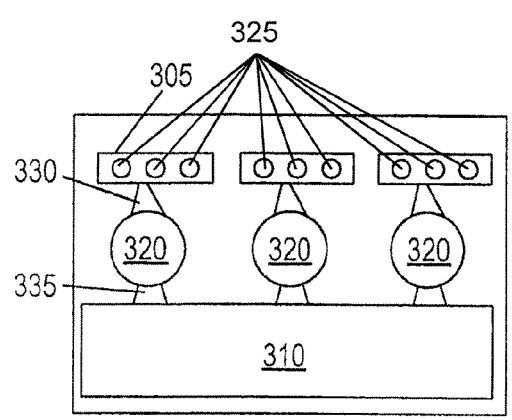
FIGS. 3A and 3B are front and side views, respectively, of an exemplary device employing chemical technology for monitoring the extent of participation in physical activity or movement by the user.
Figure 3B:
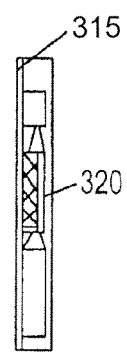

The first method to be addressed employs chemical technology whereby one or more chemicals when mixed together activate an indicator that signifies to the user participation in movement for at least a predetermined threshold, e.g., predetermined amount and/or predetermined time period. Referring to FIGS. 3A and 3B, indicator wells 305 are filled with a chemical indicator that is activated when mixed with fluid from a reservoir 310. In the illustrative example shown, the coupon includes three indicator wells 305, each having three indicator apertures 325, wherein each indicator aperture represents a different indicator (e.g., different color or indicia such as a letter or number). An impervious membrane 315 covers the surface of the device and is sealed around a pump 320 to form a vacuum. The pump 320 such a micro-pump is used to dispense fluid from reservoir 310. A fluid is selected based on such factors as its potential corrosive effects and viscosity to pass through the pump. In the exemplary embodiment three pumps 320 are shown, one associated with each well indicator 305. The application may be modified, as desired, to vary the number of indicator wells, indicator apertures and/or pumps.

Figure 3C:
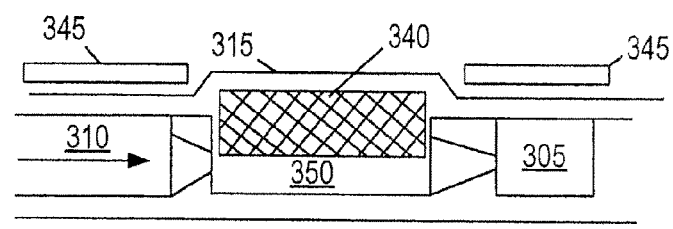
FIG. 3C is a front view of the device in FIGS. 3A and 3B with the membrane deformed.

An external force such as a motor or piezoelectric device may be used to drive the micro-pump. However, the use of a motor or piezoelectric device disadvantageously requires a power source that contributes to both the overall cost of manufacture and footprint of the integrated circuit. In a preferred embodiment, the use of a power source is eliminated altogether and instead the micro-pumps are driven by an oscillating membrane that acts as a piston. The user's motion thereby supplies the necessary force to drive the micro-pump. Accordingly, a predetermined minimum threshold level of physical activity or movement may be required to drive the micro-pump. Some physical activity or movement may be so inconsequential as to be insufficient to drive the micro-pump. Some physical or movement may be so inconsequential as to be insufficient to drive the micro-pump. As the user moves, the mass of the fluid in pumping well 350 causes the membrane 315 to vibrate or oscillate and deform, as shown in FIG. 3C. The pumping action of mass or magnet 340 may be enhanced by utilizing a changing magnetic field or a fluctuating mass. Specifically, as shown in FIG. 3C a magnetic field is created by the displacement of a magnet 340 with respect to an attracting material 345 such as steel or other magnetic material disposed proximate the pump 320. The attracting material 345 shown in FIG. 3C is configured in the shape of a metal ring. in operation, the user's motion causes the membrane 315 to vibrate or oscillate by the mass of the fluid flowing into the pumping well 350 from reservoir 310 resulting in an initial displacement of magnet 340. As the magnet 340 approaches the metal ring 345 the attraction of magnetic forces assist the suction of fluid from the reservoir 310 into the pump well 350. Gravity and motion forces the fluid into the indicator wells 305.

Reducing channels or reserve flow restrictors 330, 335 are preferable used to create a unidirectional flow of fluid from the reservoir 310 to each of the indicator wells 305. As the mass or magnet 340 is displaced in a positive y-direction a vacuum forces liquid to flow from the reservoir 310 into the pumping well. Micro-pump 320 provides metered output based on the type of movement or physical activity. The mass of magnet 340 is selected based on different activity levels. The orifice of the flow restrictors may be adjusted to accommodate a wide variety of flow rates and fluids. Fluids stored in reservoir 310 may be neutral, acidic or alkaline. The indicator in wells 305 may be a solid, fluid, gas or some combination thereof which when it mixes with the fluid from reservoir 310 is activated. In one embodiment the indicator wells activate the indicator immediately upon contact with fluid dispersed from the reservoir, irrespective of the amount of fluid. However, an alternative embodiment provides for activation of the indicator by a predetermined amount of fluid from the reservoir passing into the indicator well. This latter embodiment may be employed to signify that a period of time for participation by the user in physical activity or movement has expired. Exemplary indicators such as fluids, gels or paper that may be used include halochromic chemical compound that produce changes in compounds such as Thymol blue, Methyl red and Indigo carmine. Another class of fluid is Amylose in starch which can be used to produce a blue color in the presence of iodine. The iodine molecule slips inside of the amylose coil. Iodine is not very soluble in water, therefore the iodine reagent is made by dissolving iodine in water in the presence of potassium iodide to produce a soluble linear triiodide ion complex. The triiodide ion slips into the coil of the starch creating a blue-black color.

Figure 7A:
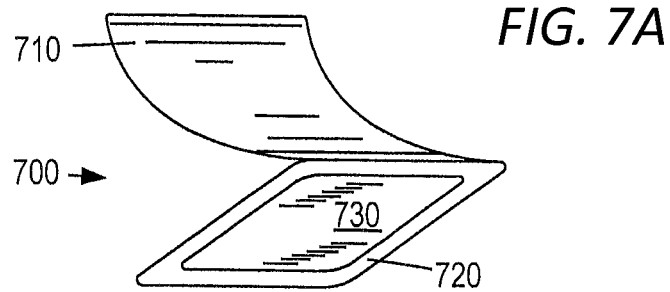
FIGS. 7A and 7B depict one embodiment of a motion-activated coupon according to the present application.
Figure 7B:
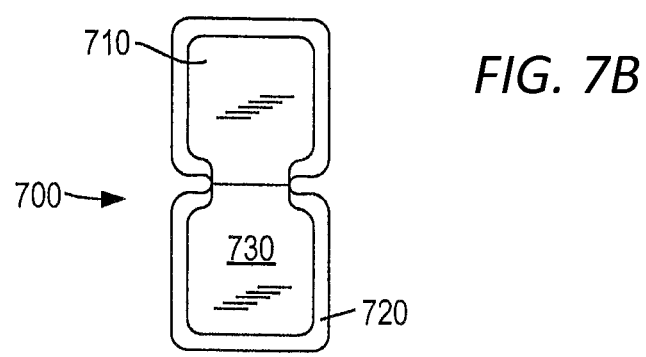

In one embodiment, the coupon comprises one or more chemical solutions that react to motion, sweat, and/or pH level of the user's skin during and after a physical activity. The chemical solutions may cause a portion of the coupon to change from one color to another. The chemical solutions may also transform an opaque overlay to a transparent overlay to reveal a layer of printed information below the layer. One example of this embodiment is depicted in FIGS. 7A and 7B. Coupon 700 has a first layer 710 which may contain a message or image and a second layer 720 with an overlay 730 that will transform from opaque to transparent upon the physical activity that activates the chemical solutions. The transparent window will then allow the user to view the message on the first layer 710.

In one embodiment, the coupon comprises two or more chemicals that react to movement of the coupon. One or more of the chemicals may be microencapsulated in small spheres and react to the second part of the solution that has an abrasive. The abrasive, with time and physical agitation, will break the encapsulated spheres and mix the two chemicals. One or more of the solutions will then change from one color to another or from an opaque overlay to a transparent overlay to reveal a layer of printed information below the overlay.

In one embodiment, the coupon comprises two gels which begin mixing when a seal separating them is broken. The physical agitation from the user will mix the two gels over a predetermined amount of time. Once the two gels have sufficiently mixed, they will then change from one color to another or from an opaque overlay to a transparent overlay to reveal a layer of printed information below the overlay.

Figure 4:
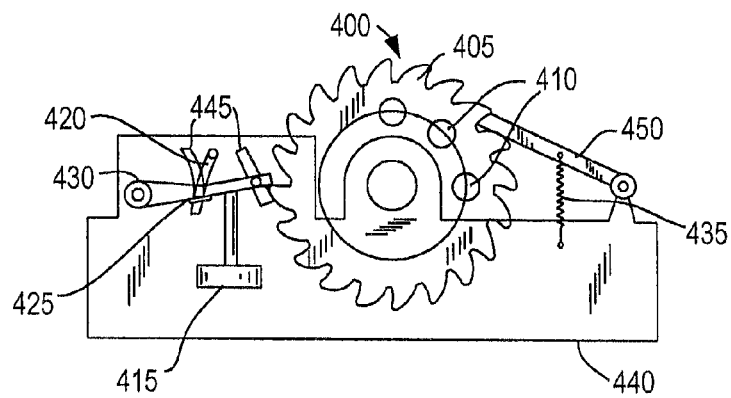
FIG. 4 is a schematic diagram of an exemplary device employing mechanical technology for monitoring the extent of participation in physical activity or movement by the user.

The next methodology to be discussed is use of the mechanical technology whereby mechanical components are displaced by forces generated by or derived from the user's motion to indicate when the user has engaged in physical activity or movement for a predetermined threshold, e.g., a predetermined amount and/or predetermined period of time. A pendulum is employed that swings when the user moves. Guides 445 serve as an escapement mechanism to restrict movement to a single direction. FIG. 4 is an exemplary assembly 400 that includes a ratchet gear 405 rotatably mounted on a base 440. A weight 415 freely supported by a level or arm 430 serves as a pendulum. The user's motion is imparted to weight 415 which, in turn, displaces the lever or arm 430 engaging a tooth of the ratchet gear 405 causing it to rotate. A rubber band 420 produces a balancing or restoring force. Hinge 425 allows the lever or arm 430 to pivot between a downward stroke position in which it engages a tooth of the ratchet gear 405 and another position a predetermined distance clear of the gear when the restoring force generated by the rubber band 420 pulls the arm back to its original position. Indicator apertures 410 may be provided to enable a mark to be visually observed by the user to signify when the user has engaged in a predetermined amount of physical activity or movement.

In the case of the present inventive kinetic coupon being utilized as an incentive for children to engage in physical activity to promote a healthier lifestyle, it is often desirable to ignore or disregard physical activity or movement by the user that is inconsequential or insignificant so as not to contribute towards the issuance or earning or rewards or points. Therefore the present application may be designed so that the motion exerted by the user is not recorded until it exceeds a predetermined threshold level. There are numerous methods in which said functionality may be accomplished an example of which will be described in further detail.

Referring once again to the mechanical assembly shown in FIG. 4, motion exerted by the user is not recorded until it overcomes or exceeds a counterbalancing static force exerted on the ratchet gear 405. This counterbalancing static force may be produced by a tension spring 435, a magnet or other device. Rotation of the ratchet gear 405 is restricted by a restricting arm 450 which is pivotally mounted to base 440. The tension spring 435 is connected between the base and restricting arm 450. When the user's motion overcomes or exceeds the counterbalancing static force produced by the tension spring physical activity or movement is recorded.

Figure 8A:
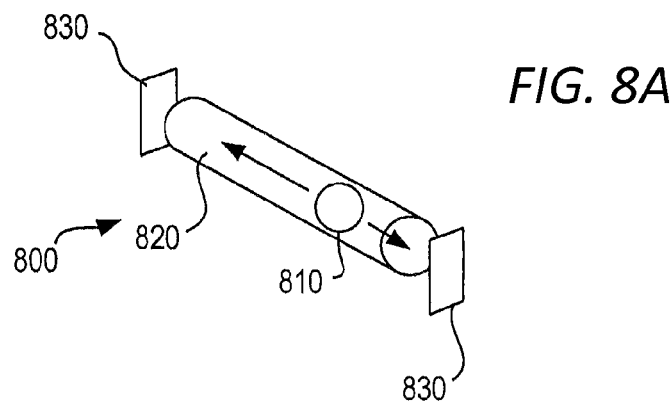
FIG. 8A shows a motion sensor in which a magnetic ball is held by magnetic attraction between contacts in a tube, in accordance with one embodiment of the present invention.

In one embodiment, the coupon comprises a kinetic device as a sensor which comprises a magnetic switch. The magnetic switch may include a conductive object such as, for example, a metal ball which is held in place in an area by magnetic attraction. If the force is strong enough the object will overcome the magnetic force of the object, which will move to either end of the area and short against two contacts at the boundaries of the area. The shorted contacts may be periodically sampled to assess physical activity. FIG. 8A depicts one example of this a motion sensor 800 according to this embodiment in which the magnetic ball 810 is held by magnetic attraction between the contacts 830 in the tube 820.

In one embodiment, a coupon comprises a microprocessor which periodically samples the contacts in a motion detector to determine when contact has been made. The sample rate may be adjusted by adjusting the internal timer. The microprocessor may also be set to turn on when there is a transition on the contacts and turn off when no motion is detected to conserve power. The battery may be shipped in the unit. A power switch will trigger the unit on. The power can be automatically turned off by the processor or can be enabled for a preset duration. A capacitor is used to keep the power switch on. Over time the voltage on the capacitor is bled off with a high value resistor. If the processor wishes to stay alive the processor can recharge the voltage on the capacitor.

Figure 20:
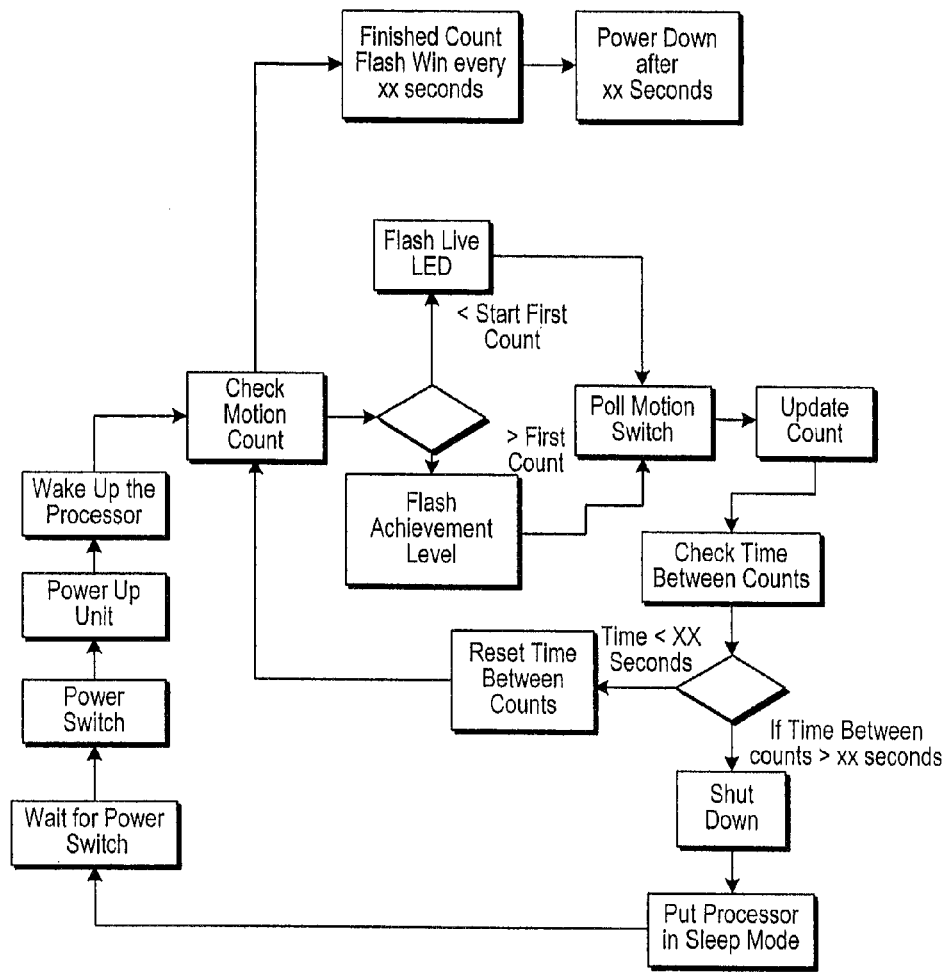
FIG. 20 depicts a flow diagram of one embodiment of a method of conserving power according to the present application.

In one embodiment as depicted in FIG. 20, the software on the microprocessor has two main loops that run. The first loop is the power loop. In this loop the unit is powered up from the power switch. The unit then processes the second loop, which tracks movement. When movement is not detected the unit within a predetermined number of seconds of use it will go back to sleep. The unit will wake up if motion is detected on the motion detect switch or the power switch is depressed.

Figure 8B:
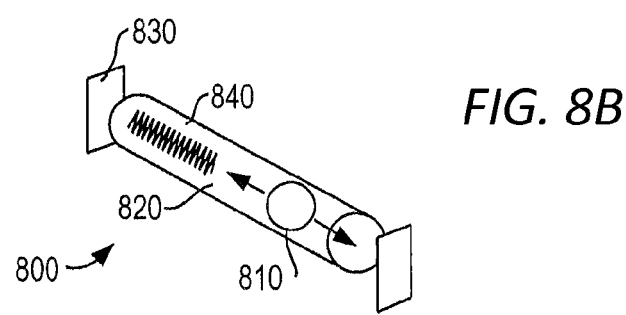
FIG. 8B shows a motion sensor having a conductive object and a coil inside a conductive tube, in accordance with one embodiment of the present invention.

In one embodiment, the coupon includes a motion sensor composed of a conductive tube inside of which resides a conductive object such as a ball and a coil. FIG. 8B depicts a motion sensor 800 according to one example of this embodiment. One end of the tube 820 contains an electrical contact 830 insulated from the tube. A coil 840, compression spring, or other compressible, non conductive material rests on the insulted portion of the electrical contact 830 located in the end of the insulted tube 820 and holds the conductive ball 810 from the end of the conductive tube 820. Upon sensing motion, the ball 810 deflects inside tube 820 in the general direction of the motion. This compresses the spring 840 and, if the motion is of sufficient magnitude, causes the ball 810 to come in contact with the contact 830 at the end of the conductive tube 820. Coming in contact with the electrical contact 830 in the end of the tube 820 causes an electrical circuit to be made. This circuit signal is interpreted by control electronics indicating that motion has occurred. The circuit signal may include a electronic circuit that incorporates algorithms capable of detecting individual deflections and interprets the inputs to correspond to the use, orientation and numeric quantity of deflections detected. The electronics interpret the information and send the results to a storage or enunciation device which may include a display such as, for example, liquid crystal display, light emitting diode display or other means to store or communicate the resulting information to a user.

Figure 8C:
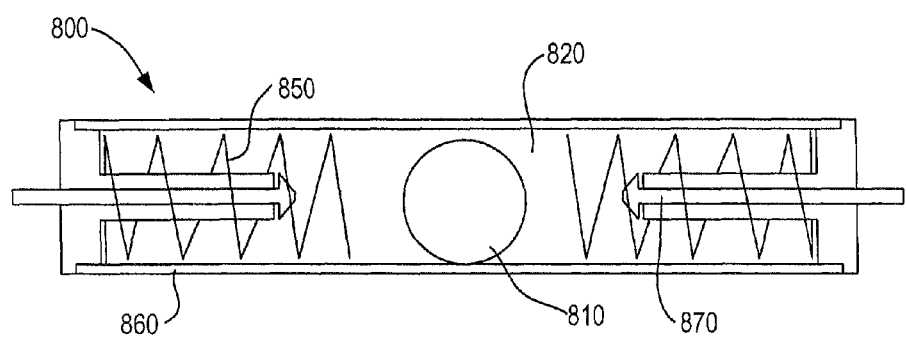
FIG. 8C shows a motion sensor having a conductive ball housed in a conductive tube between two springs, in accordance with one embodiment of the present invention.

In one embodiment, the coupon comprises a spring-loaded ball and multiple contact tube motion detector. The motion sensor may be composed of a conductive tube inside of which resides a conductive ball. Each end of the tube contains an electrical contact insulated from the tube. Two coil compression springs or other compressible material rest on the insulated portion of the electrical contact located in the end of the insulated tube and hold the conductive ball equidistant from the ends of the conductive tube. Upon sensing motion, the ball deflects inside tube in the general direction of the motion. This compresses the spring and, if the motion is of sufficient magnitude, causes the ball to come in contact with the contact at the end of the conductive tube. Coming in contact with the electrical contact in the end of the tube causes an electrical circuit to be made. This circuit signal is interpreted by control electronics indicating that motion has occurred. One example of this embodiment is depicted in FIG. 8C. The conductive ball 810 is housed in the conductive tube 860 between two springs 850. The springs surround two conductive posts 870 and hold the conductive ball 810 away from the two conductive posts 870 while the motion detector 800 is standing still. Motion of the motion detector 800 will force the conductive ball 810 against one of the springs 850 which will compress and allow the conductive ball to touch one of the conductive posts 870 which completes a circuit with the conductive tube 860. Each time a circuit is completed, the circuitry of the coupon implements a counter until the predetermined threshold is reached.

Figure 9:
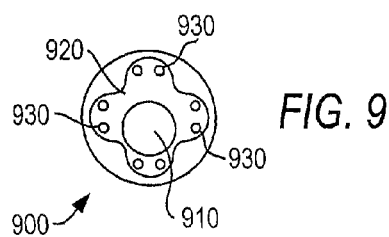
FIG. 9 shows a dual-axis motion sensor having a ball in a cross-shaped channel, in accordance with one embodiment of the present invention.

In one embodiment, the coupon comprises a dual-axis motion sensor with a ball in a cross-shaped channel. One example of this embodiment is depicted in FIG. 9. In this embodiment, the motion sensor 900 comprises a conductive sphere 910 and rests inside a cross-shaped channel 920. The shape of the channel fixes the potential movement of the ball 910 to two axes. At the end of each of the four channels there is an electronic contact 930 that closes a circuit whenever the ball 910 makes contact. The cross-shaped channel form and orientation to the device is defined by the orientation and the allowed movement.

Figure 10:
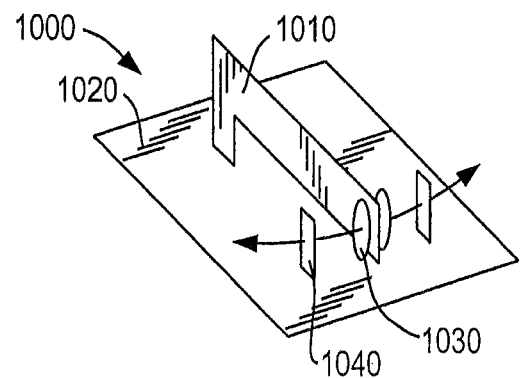
FIG. 10 shows a single-axis motion sensor in which a conductive flat spring has one end affixed to a conductive member with a weight on the other end to amplify detected motion, in accordance with one embodiment of the present invention.

In another embodiment, the coupon comprises a single-axis motion sensor. One example of this embodiment is depicted in FIG. 10. The motion sensor 1000 is comprised of a single conductive flat spring 1010 in which one end is affixed to a circuit board 1020 or other conductive member and the other end contains a weight 1030 to amplify detected motion. Conductive stops 1040 are affixed to the circuit board 1020 and are equally spaced on either side of the flat spring 1010 and weights 1030. Upon deflection, the conductive flat spring 1010 contacts conductive stops 1040. When contact with the conductive stops 1040 occurs, a signal flows through the circuit board 1020 or other conductive member to the sensor then to the conductive stops and back through the circuit board. This signal is interpreted by control electronics indicating that motion has occurred. The conductive stops may be electrically joined or remain separate wherein the control electronics may interpret the signal received from the motion detector together or individually.

Figure 11:
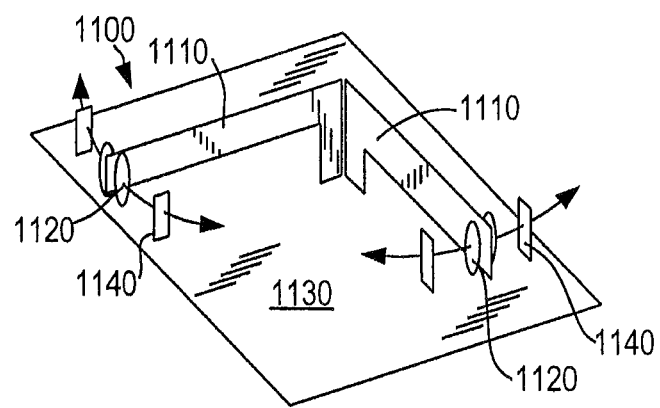
FIG. 11 shows a dual-axis motion sensor in which a single conductive flat spring is bent to form an angle between 1 and 90 degrees and in which each end of the conductive flat spring incorporates a weight to amplify detected motion, in accordance with one embodiment of the present invention.

In one embodiment, the coupon comprises a dual-axis motion sensor comprised of a single conductive flat spring bent to form an angle of between 1 and 90 degrees. One example of this embodiment is depicted in FIG. 11. Each end of the flat spring 1110 incorporates a weight 1120 to amplify detected motion. The bent end of the sensor 1110 is affixed to a circuit board 1130 or other conductive member. Conductive stops 1140 are affixed to the circuit board and are equally spaced on either side of the flat springs 1110 and weights 1120. When contact with the conductive stops 1140 occurs, a signal flows through the circuit board 1130 or other conductive member to the sensor then to the conductive stops 1140 and back through the circuit board 1130. This signal is interpreted by control electronics indicating that motion has occurred. Each of the four conductive stops 1140 may be electrically joined or remain separate. Therefore, the control electronics may interpret the signal received from the motion detector 1100 together or individually. In this embodiment, the motion detector may include an electronic circuit that incorporates algorithms capable of detecting and interpreting individual or joined signals from the motion sensor. The electronics can define orientation, number of deflections from each conductive stop and interpret the results. The resulting information is maintained in electrical storage or displayed on an enunciation device which may include a Liquid crystal display, Light emitting diode display or other means to store or communicate the resulting information to a user.

Figure 12:
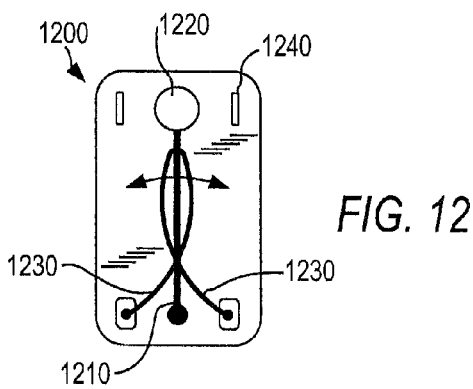
FIG. 12 shows a motion sensor having a dual-axis or balanced pendulum motion detector in which a pendulum pivots at one end and contains a weight at the other, and in which two balanced hair pin springs are symmetrically located around a long axis of the pendulum, in accordance with one embodiment of the present invention.

In one embodiment as depicted in FIG. 12, the coupon comprises a motion sensor having a dual-axis or balanced pendulum motion detector 1200 composed of a pendulum 1210 which pivots at one end and contains a weight 1220 at the other, and which incorporates two balanced hair pin springs 1230 symmetrically located around the long axis of the pendulum 1210. The hair pin springs 1230 balance the pendulum 1210 in a central location and allow deflection in two directions. Two contacts 1240 are located at either side of the pendulum weight 1220. Deflection of the pendulum 1210 to either contact 1240 causes an electrical circuit to be completed between the pivot end of the pendulum 1210 through the weight 1220 to either contact 1240. The contacts 1240 may be joined or separated. The pendulum 1210 may include electronic logic. This embodiment may further comprise an electronic circuit that incorporates algorithms capable of detecting individual or joined deflections and interpreting the inputs to correspond to the use, orientation and numeric quantity of deflections detected. The electronics interpret the information and send the results to a storage or enunciation device which may include a Liquid crystal display, Light emitting diode display or other means to store or communicate the resulting information to a user.

Figure 13:
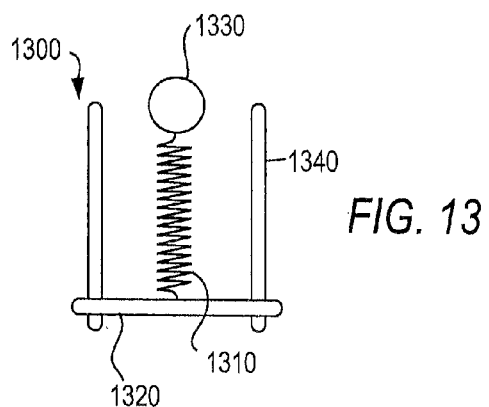
FIG. 13 shows a three-axis motion sensor in which a conductive spring wire is affixed to a mounting plate at one end and has a weight at the other end that protrudes through a conductive hoop, in accordance with one embodiment of the present invention.

In one embodiment as depicted in FIG. 13, the coupon comprises a motion detector 1300 comprising a spring wire 1310 with a dampening device motion detector. This embodiment includes a three-axis motion sensor 1300 in which a conductive spring 1310 wire is affixed to a selectively conductive mounting plate 1320 (such as a printed circuit board) and the other end incorporates a fixed weight 1330. A predetermined length of the spring wire 1310 protrudes through a compressible material (such as open cell foam). The fixed weight end 1330 protrudes through a conductive hoop 1340. The hoop 1340 is connected to the mounting plate 1320. Upon deflection, the conductive spring wire 1310 deflects and contacts the conductive hoop 1340. When contact with the conductive hoop 1340 occurs, a signal flows through the printed circuit 1320. This signal is interpreted by control electronics indicating that motion has occurred. The conductive hoop may be electrically joined or remain separate wherein the control electronics may interpret the signal received from the motion detector. This embodiment may include electronic logic such as, for example, an electronic circuit that incorporates algorithms capable of detecting individual deflections and interpreting the inputs to correspond to the numeric quantity of deflections detected. The electronics send the resulting information to a storage or display device such as, for example, a liquid crystal display, light-emitting diode display or other means to store or communicate the resulting information to a user.

In one embodiment, the coupon comprises a spring wire with dampening device motion detector and three-axis interpretation. This embodiment includes a three-axis motion sensor in which a conductive spring wire is affixed to a selectively conductive mounting plate (such as a printed circuit board) and the other end incorporates a fixed weight. A predetermined length of the spring wire protrudes through a compressible material (such as open cell foam). The fixed weight end is located between two individual contacts. A third contact is located on the selectively conductive mounting plate under the weight. Upon sensing motion, the spring wire is deflected and contacts one or more of the conductive contacts. An electrical signal flows through the selectively conductive mounting plate. This signal is interpreted by control electronics indicating that motion has occurred. The conductive stops may be electrically joined or remain separate wherein the control electronics may interpret the signal received from three contacts and the motion detector. The compressible material dampens oscillations from the spring wire. This motion detector may include an electronic circuit that incorporates algorithms capable of detecting individual deflections and interpreting the inputs which correspond to the use, orientation and numeric quantity of deflections detected. The electronics interpret the information and send the results to a storage or enunciation device which may include a Liquid crystal display, Light emitting diode display or other means to store or communicate the resulting information to a user.

In one embodiment, the coupon includes a motion detector that can detect 360 degrees of longitudinal motion and which is comprised of a platform with a single outer raised conductive ring, an inner conductive surface placed inside, but not contacting the raised conductive ring, a movable ball or "puck" is located inside the raised conductive ring, and a compressible porous member such as open cell foam, which fits around the movable ball or "puck" and which is compressed by the ball or "puck" as it is deflected by motion. The ball or "puck" is held in a central location by the compressible porous member. Upon sensing motion, the ball or "puck" is deflected and causes the porous member to compress in the direction the motion is detected and proportion to the energy contained in the motion. If the energy is sufficient, the porous member if fully compressed and the ball or puck makes contact through the porous member to the raised conductive ring. Making contact with the raised conductive ring caused an electrical circuit to be completed. This embodiment may include an electronic circuit that incorporates the algorithms capable of detecting deflections and interpreting the inputs to correspond to the use, orientation and numeric quantity of deflections detected. The electronics can define orientation, number of deflections from each conductive stop and interpret the results. The resulting information is maintained in electrical storage or displayed on a display device such as, for example a liquid crystal display, light-emitting diode display or other means to store or communicate the resulting information to a user.

Figure 14:
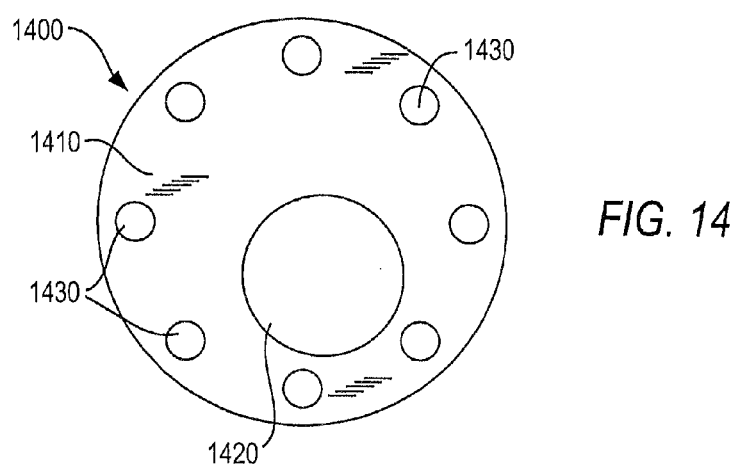
FIG. 14 shows a motion sensor having raised conductive ring members arranged equidistant from a center point and mounted on a platform, with a movable puck located inside the raised conductive ring members, in accordance with one embodiment of the present invention.

In one embodiment as depicted in FIG. 14, the coupon includes a motion sensor 1400 comprising separate or individual raised conductive ring members 1430 arranged equidistant from a center point and mounted on a platform 1410, an inner conductive surface is located on the platform but not touching the raised conductive ring members 1430, a movable ball 1420 or "puck" is located inside the individual raised conductive ring members 1430, and a compressible porous member which fits around the movable ball 1430 or "puck" and which is compressed by the ball 1430 or "puck" as it is deflected by motion. The ball 1430 or "puck" is held in a central location by the compressible porous member. Upon sensing motion, the ball 1430 or "puck" is deflected and causes the porous member to compress in the direction the motion is detected and proportion to the energy contained in the motion. If the energy is sufficient, the porous member if fully compressed and the ball 1430 or puck makes contact through the porous member to one or more of the individual raised conductive ring members 1430. Making contact with one or more individual raised conductive ring members 1430 caused an electrical circuit to be completed. This motion sensor 1400 may include a electronic circuit that incorporates algorithms capable of detecting individual or joined deflections and interpreting the inputs to correspond to the use, orientation and numeric quantity of deflections detected. The electronics send the resulting information to a storage or enunciation device which may include a Liquid crystal display, Light emitting diode display or other means to store or communicate the resulting information to a user.

Figure 15A:
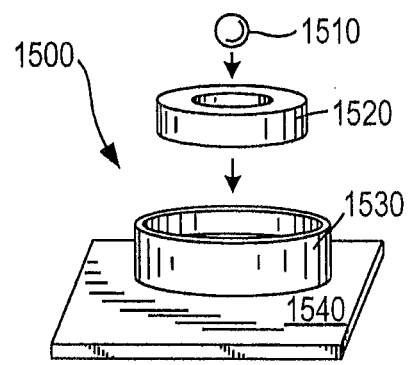
FIG. 15A shows a motion sensor having a conductive element such as a ball, a dampening element such as a foam ring, and a conductive ring disposed on a substrate, in accordance with one embodiment of the present invention.
Figure 15B:
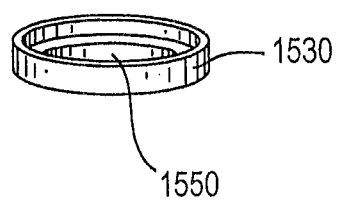
FIG. 15B shows the motion sensor of FIG. 15A with the conductive ring surrounding an inner conductor, in accordance with one embodiment of the present invention.
Figure 15C:
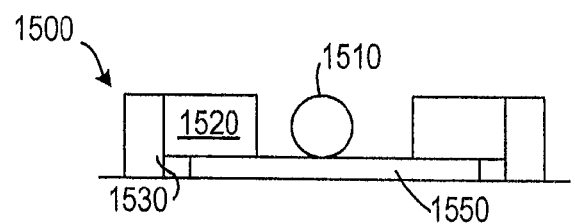
FIG. 15C shows a cross-section of the motion sensor of FIG. 15A with the ball resting on the inner conductor and held apart from the conductive ring by the foam ring, in accordance with one embodiment of the present invention.
Figure 15D:
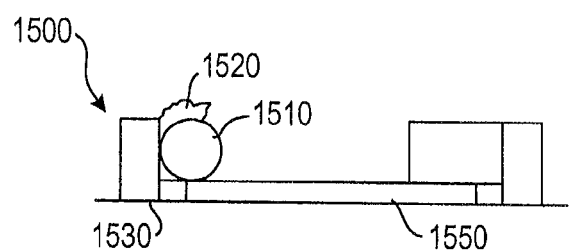
FIG. 15D shows the cross-section of the motion sensor of FIG. 15A with motion causing the ball to be forced against the foam ring so as to deform the foam ring and form a circuit between the inner conductor and the conductive ring, in accordance with one embodiment of the present invention.
Figure 15E:
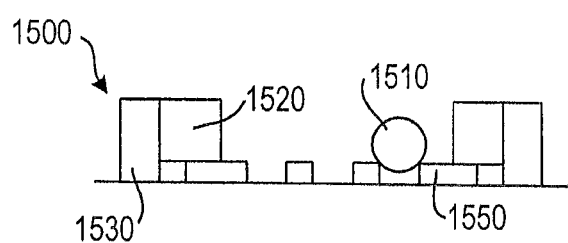
FIG. 15E shows the cross-section of the motion sensor of FIG. 15A in which the inner conductor has channels, holes, or protuberances which inhibit free movement of the ball, in accordance with one embodiment of the present invention.

As depicted in FIGS. 15A, 15B, 15C, 15D, and 15E, one embodiment of the present application comprises a coupon including a motion detector 1500 comprising a conductive element such as a ball 1510, a dampening element such as a foam ring 1520, and a conductive ring 1530 disposed on a substrate 1540. The conductive ring 1530 surrounds an inner conductor 1550. A cross-section of this motion detector 1500 is depicted in FIG. 15C which shows the ball 1510 resting on the inner conductor 1550 and held apart from the conductive ring 1530 by the foam ring 1520. As depicted in FIG. 15D, motion of the motion detector will force the ball 1510 against the foam ring 1520, deforming the foam ring 1520 and forming a circuit between the inner conductor 1550 and the conductive ring 1530. In a further embodiment depicted in FIG. 15E, the inner conductor 1550 may have channels, holes, or protuberances which inhibit the free movement of the ball 1510 and thus require additional motion to form a circuit.

Figure 16:
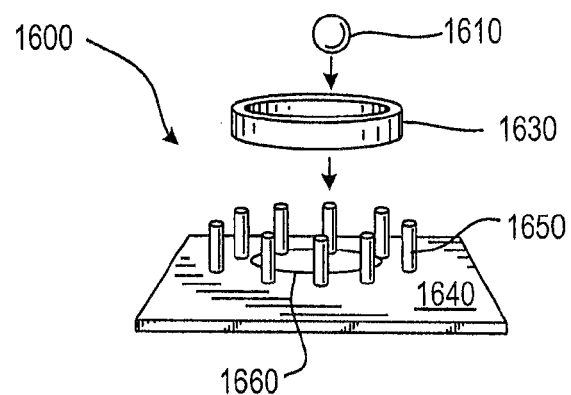
FIG. 16 shows a motion sensor in which a conductive element such as a ball is disposed in a dampening element such as a foam ring which is placed inside a number of conductive posts on a substrate, in accordance with one embodiment of the present invention.

A similar embodiment of a motion detector 1600 is depicted in FIG. 16 in which a conductive element such as a ball 1610 is disposed in a dampening element such as a foam ring 1630 which is placed inside a number of conductive posts 1650 on a substrate 1640. An inner conductor 1660 is disposed in the middle of the motion detector 1600. In this embodiment, the ball 1610 forms a circuit between the conductive posts 1650 and the inner conductor 1660 when the ball 1610 is subject to sufficient motion to deform the foam ring 1630 and allow the ball 1610 to contact the conductive posts 1650 while resting on the inner conductor 1660.

Figure 17:
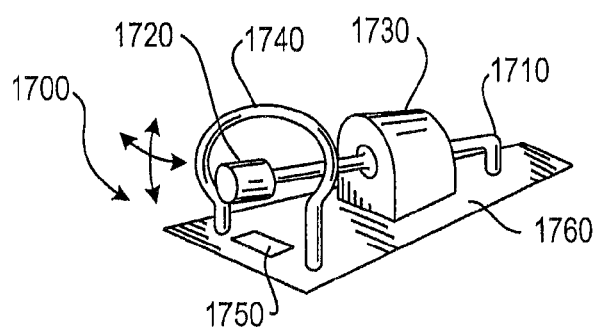
FIG. 17 shows a motion sensor in which a conductive pin has a weight coupled to its end with the weight surrounded by a conductive member and/or conductive plate, in accordance with one embodiment of the present invention.

FIG. 17 depicts another embodiment of a motion detector 1700 to be included with a coupon according to the present application. The motion detector 1700 comprises a conductive pin 1710 that may have a weight 1720 coupled to the end. The conductive pin 1710 may be surrounded by a dampening element such as a piece of foam 1730 which may be coupled to the substrate 1760 from which the conductive pin 1710 extends. The weight 1720 is surrounded by a conductive member 1740 and/or a conductive plate 1750. The movement of the motion detector 1700 will cause the weight 1720 to contact either the conductive member 1740 or the conductive plate 1750, closing a circuit with the conductive pin 1710.

Figure 18A:
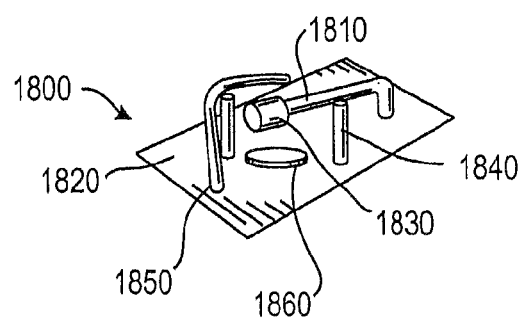
FIG. 18A shows a motion sensor in which a conductive pin has a weight at its end with the weight surrounded by conductive posts and positioned above a conductive plate, in accordance with one embodiment of the present invention.
Figure 18B:
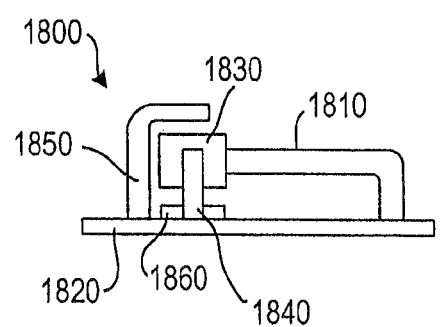
FIG. 18B shows a side-view of the motion sensor of FIG. 18A, in accordance with one embodiment of the present invention.

A similar embodiment is depicted in FIG. 18A. In this embodiment of a motion detector 1800, a conductive pin 1810 with a weight 1830 extends from a substrate 1820. The weight 1830 is surrounded by a plurality of conductive posts, 1840, 1850 and positioned above a conductive plate 1860. Motion cause the conductive pin 1810 to contact either the posts 1840, 1850 or the conductive plate 1860 which completes a circuit. A side view of this embodiment is depicted in FIG. 18B.

Figure 19:
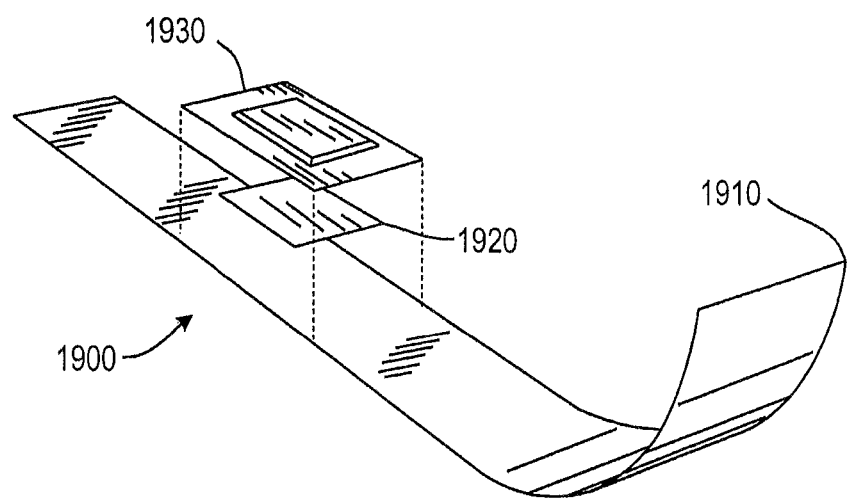
FIG. 19 depicts one embodiment of a coupon according to the present application coupled to a wearable device.

One embodiment of a coupon is depicted in FIG. 19. The coupon 1900 comprises a flexible band 1910, a circuit 1920 which includes a motion detector, and a housing 1930 which holds the circuit 1920 to the flexible band. The flexible band 1910 may further comprise an adhesive strip on one or both ends in order to affix the coupon 1900 to a user. In some embodiments, the housing may be a pocket in the band and not a separate component. In another embodiment, the housing may also be coupled to the sensor and then affixed to the band.

In one embodiment, the coupon comprises a motion detector comprised of individual contacts arranged on a sliding surface and which are spaced equidistant from a center point and which alternate in conductivity. A ball or puck is contained inside the contacts and which upon being tilted, slides against the contacts and creates a circuit. The sensor can detect tilts at 45 degree quadrants.

Figure 21:
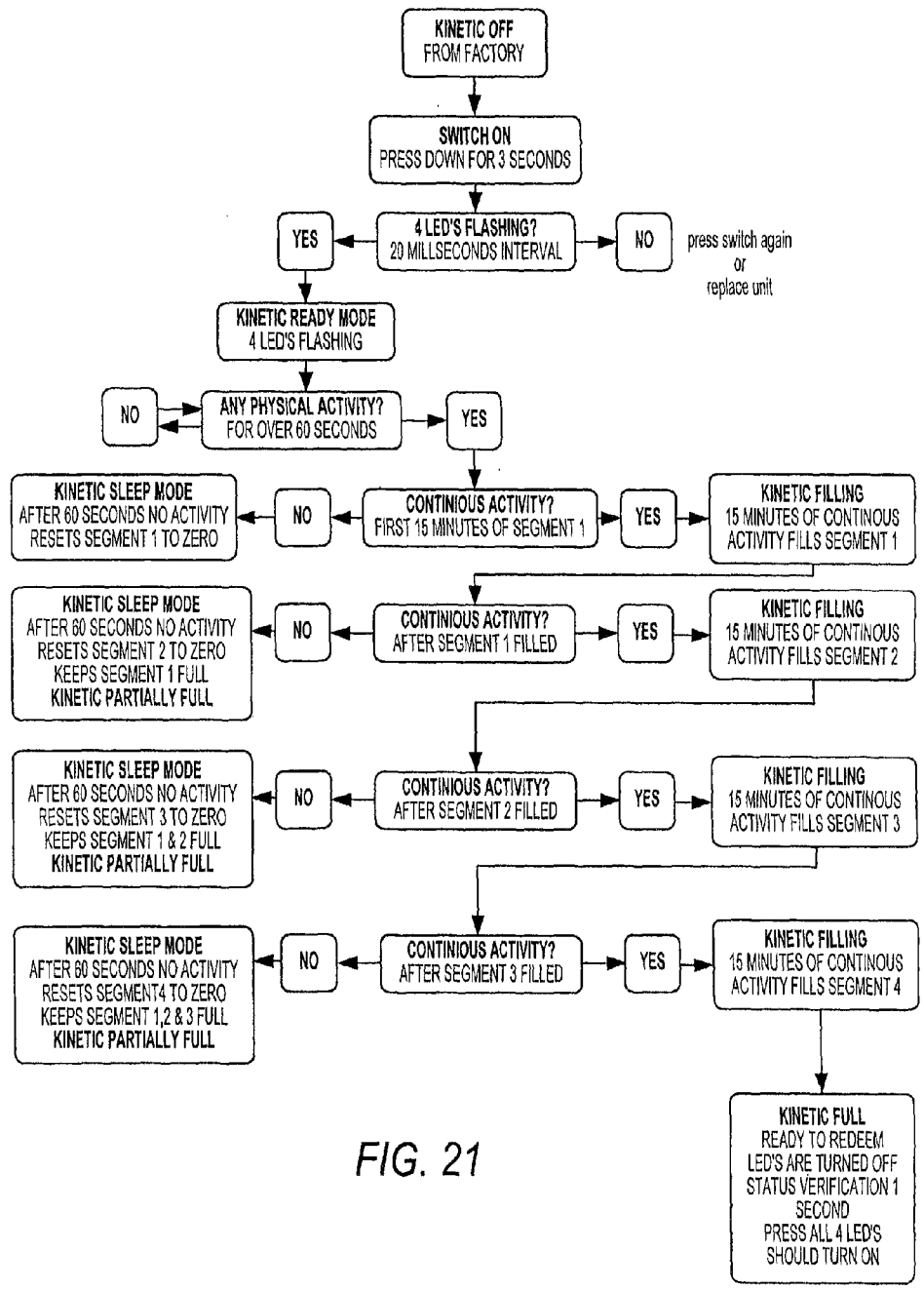
FIG. 21 depicts a flow diagram of a method according to the present application.

In one embodiment, a coupon comprises a series of light emitting diodes which provide signals to a user. One embodiment of a method of measuring physical activity and conserving battery power of a coupon is depicted in FIG. 21.

Intelligence may be built into a coupon such that the coupon does not begin to measure physical activity until a predetermined time has passed. Thus, the coupon is not activated until a predetermined time. This may be advantageous when a number of coupons are presented to a user, such as in a physical therapy application where the user is given a number of coupons that must be activated at different times. The activation of certain coupons at different times will prevent the user from wearing all of the coupons at the same time.

In one embodiment, the coupon may also serve as a gift card. The gift card would be purchased for a fixed dollar amount. Typical of traditional gift cards, the gift card may be redeemed for the purchased value or if the consumer chooses to engage in physical activity for a predetermined level or amount of time, the gift card may increase in value. Suppose one purchases a gift card from a book store for $20 and gifts the card to someone. This individual may choose to use the gift card to purchase merchandise for the value of $20 or may choose to engage in physical activity to increase the value of the gift card (perhaps the gift card will increase in value from $20 to $25).

In one embodiment, the coupon comprises a ring motion detector with equidistant non-alternating contacts. The motion detector is comprised of individual contacts arranged on a sliding surface and which are spaced equidistant from a center point and which do not alternate in conductivity (i.e. ++, --). A ball or puck is contained inside the contacts and which upon being tilted, slides against the contacts and creates a circuit. The sensor can detect tilts at 90 degree quadrants.

In one embodiment, the coupon comprises a ring motion detector with equidistant pairs of alternating contacts. The motion detector is comprised of pairs of contacts arranged on a sliding surface and which are spaced equidistant from a center point and the contact of which alternate in conductivity. A ball or puck is contained inside the contacts and which upon being tilted, slides against the contacts and creates a circuit. The sensor can detect tilts at 45 degree quadrants. Space between alternating contacts changes speed and transition of the ball or puck from one set of contacts to the other.

In one embodiment, the coupon comprises a motion detector comprised of pairs of contacts arranged on a sliding surface and which are spaced equidistant from a center point and the contact of which do not alternate in conductivity. A ball or puck is contained inside the contacts and which upon being tilted, slides against the contacts and creates a circuit. The sensor can detect tilts at 90 degree quadrants.

In either of the ring designs described above, a hole may exist in the center of the ring surface (i.e. printed circuit board). This will allow the ball or puck to remain idle or in a stationary position during a time when the motion detector should not be registering hits (i.e. during transportation).

In another embodiment, the motion detector is comprised of pairs of electrical contacts arranged around the circumference of a sliding surface. A plurality of holes or protuberances are incorporated into the sliding surface. A conductive object such as, for example, a sliding puck or rolling ball, touches the electrical contacts upon tilting of the motion detector and creates electrical contact between the contacts. The holes or protuberances in the sliding surface alter the friction between the conductive object and the surface thereby adjusting the reaction of the conductive ball or puck to tilting. When the conductive object contacts one or more of the electrical contacts, a circuit is formed between the contacts and the contact is recorded by a device.

Figure 5:
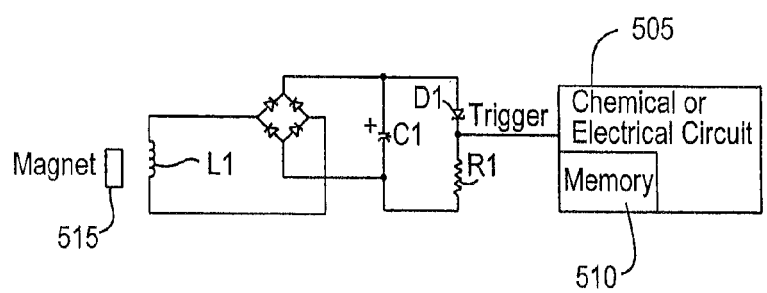
FIG. 5 is a schematic diagram of an exemplary device employing electrical technology for monitoring the extent of participation in physical activity or movement by the user.

A final and third methodology for monitoring the user's motion is achieved using electrical technology, as shown in FIG. 5. In accordance with this third method electrical energy is captured by moving a magnet 515 around or through a coiled wire. A change in the magnetic field includes an electromotive force or voltage in inductor L1. Four diodes denoted as D1 represent a bridge rectifier to convert the AC voltage generated in inductor L1 to DC voltage for storage by a capacitor C1. Similar to that described above with respect to the other methodologies, the electrical methodology also disregards physical activity or movement by the user which is inconsequential or insignificant (falls below a predetermined threshold level). To achieve this result, a triggering signal is transmitted to power ON a chemical or electrical circuit 505 only when the stored voltage in capacitor C1 exceeds a predetermined threshold voltage level of physical activity or movement. In the ON state, the voltage is used to power an electronic circuit that electronically records the level of physical activity in memory 510 and change the pH of a compound of a chemical indicator thereby producing a color to signify to the user that the kinetic coupon has been validated or activated and is now redeemable.

It is to be noted that each of the methodologies described above may be used independently or in any combination thereof.

Many additional features may be added to the inventive kinetic coupon. A timing clock may be employed to ensure that the kinetic coupon is validated and/or redeemed after being validated prior to expiration of a predetermined redemption period of time. Upon the expiration of the predetermined redemption period of time, the kinetic coupon if not yet validated will no longer be activatable and, if already validated, will become inactive or perhaps indicate on the display that it is no longer redeemable.

The kinetic coupon may be reusable whereby after validation and redemption the components may be reset and used again. Otherwise, it is also contemplated and within the intended scope of the application for all or some portion of the kinetic coupon to be disposable. One factor in this determination is the overall cost associated with the components of the kinetic coupon itself.

As previously noted, the kinetic coupon may be designed or customized, as desired, to promote the specific corporation or sponsor. For example, the name, trademark, logo, or other indicia of the corporation or sponsor may be displayed on the strap or other portion of the coupon including in the display itself. In this regard, the kinetic coupon may be used as yet another advertising tool for promotion of a corporate or sponsor's name, brand, and/or product/service. Additional companies or advertisers may be added to the kinetic coupon.

Figure 6:
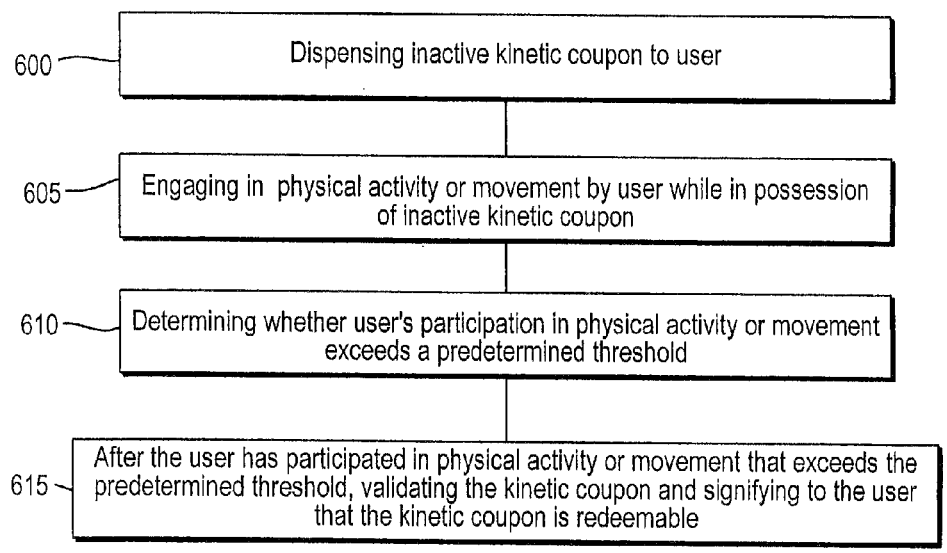
FIG. 6 is an exemplary flow chart of the use of the kinetic coupon in accordance with the present application.

FIG. 6 is an exemplary flow chart of the user of the kinetic coupon in accordance with the present application. In step 600 in inactive coupon is dispensed to the user. Initially, the kinetic coupon is not activated and this not redeemable for any type of reward or incentive. However, the indicia may display instructions that invite the user to participate in physical activity or movement while in possession of the inactive kinetic coupon in step 605. A determination is made in step 610 whether the user's participation in physical activity exceeds a stored predetermined threshold, e.g., a predetermined amount of physical activity and/or a predetermined period of time. After the user has participated in physical activity for at least the predetermined threshold then in step 615 the kinetic coupon is validated and signifies to the user that it is now able to be redeemed.

In one embodiment, the coupon comprises a system for encouraging physical activity in children. In this embodiment, a child is issued a coupon from a source which may be the child's parents, the child's school, or an entity such as a restaurant or other vendor. The parent or guardian of the child may set up an account such as, for example, a bank account or a points account for the child on a web site. When the child engages in physical activity that exceed the predetermined threshold set by the coupon, the coupon will success to the child with an indicator such as a code. The code may then be entered into the web site by the parent or guardian or by the child to redeem the coupon for a predetermined amount of points or currency. In the embodiment where an online bank account is set up for the child, the coupon may be redeemed for currency which is deposited into the child's account.

In one embodiment, a coupon according to the present application comprises a self-contained game that monitors the physical activity of a user and provides feedback to the user based on the level of physical activity of the user. The game will react to the physical activity of the user and issue points or rewards to the user based on the level of physical activity recorded by the coupon.

One example of this embodiment is a virtual pet that is displayed on a display such as a liquid crystal display on the coupon. The virtual pet will appear as healthy when the coupon has detected a predetermined amount of physical activity from the user and the virtual pet may appear ill if the coupon detects an amount of physical activity below a threshold level. The pet may also grow and become stronger upon detection of a number of different thresholds of physical activity. In a further embodiment, the coupon monitors only recent physical activity from a predetermined time in the past until the present. This ensure that the user regularly engages in physical activity to maintain the health of the virtual pet.

In one embodiment, the coupon interacts with an online game which responds to the amount of physical activity detected by the coupon. Such a game may reward the user upon the detection of certain threshold levels of physical activities from the coupon.

In one embodiment, a coupon according to the present invention may be issued as a label on food or beverage products, a peel-off addition to packaging of goods, or a promotional label that may be sold in office supply stores and printed with a company's promotional logo.

In one embodiment a device including a coupon has a removable component that alerts the user when a predetermined level of physical activity has been reached. The removable component has a display or other visual indication as described herein to inform the user how much physical activity has been achieved while wearing the device and/or whether the predetermined level of physical activity has been reached. The removable component may fit into a device such as a wearable bracelet, anklet, or other device as described herein. The removable component records the amount of physical activity detected by a motion sensor in the removable component.

The removable component may be added to a second device such as, for example, a toy that is able to detect the amount of physical activity recorded by the removable component or some other signal from the removable component corresponding to the amount and/or level of physical activity recorded. The second device reacts to the amount and/or level of physical activity recorded by the removable component in one or more ways such as, for example, activating the features of the second device for a predetermined period of time or unlocking special features upon detection of a certain amount and/or level of physical activity recorded by the removable component.

One example of a device with a removable component that may be used with a second device is a bracelet with a removable component configured to record an amount of physical activity undertaken by the user while wearing the bracelet that is detected by the bracelet. The user may remove the removable component from the bracelet and insert the removable component into a video game console, which will allow the user to play video games only if a predetermined amount and/or level of physical activity has been recorded by the removable component. The video game console may provide bonuses to a user such as, for example, additional playing time or additional available games, if a certain amount and/or level of physical activity has been recorded. In one embodiment, the video game console will allow playing time commensurate with the time of physical activity recorded by the removable component.

Figure 22:
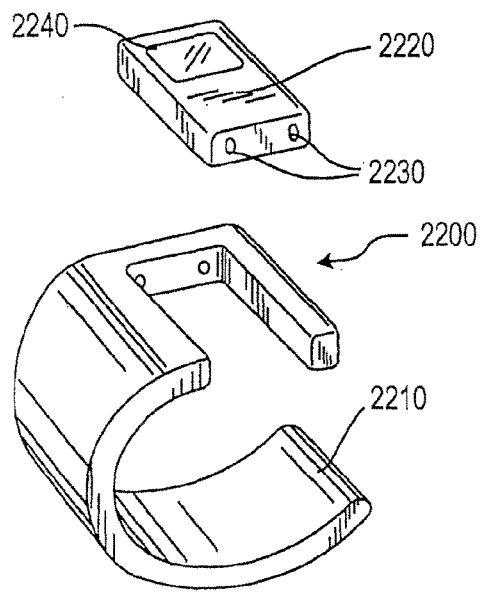
FIG. 22 depicts an embodiment of a device according to the present invention with a removable component that records physical activity detected by the device.
Figure 23:
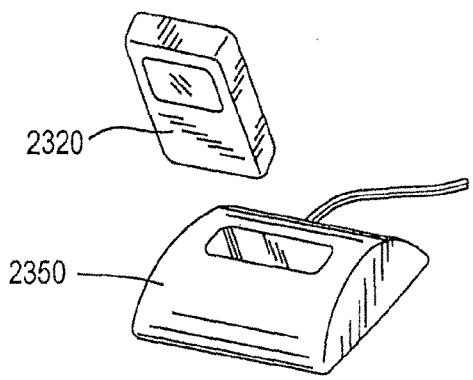
FIG. 23 depicts the removable component shown in FIG. 22 as inserted into a base with a communication cable.
Figure 24:
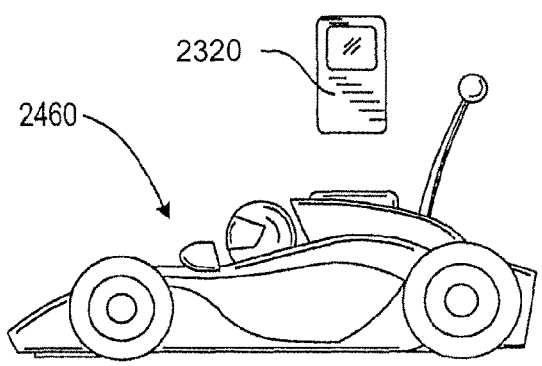
FIG. 24 depicts the removable component showing in FIG. 22 being inserted into a toy.

One example of a removable component is depicted in FIGS. 22, 23, and 24. A first device 2200 includes a wrist strap 2210 to be worn by a user. The first device 2200 further includes a motion sensor and a removable component 2220 for recording the physical activity of a user wearing the first device 2200 as detected by the motion sensor. The removable component further includes a display 2340 to alert the user when a predetermined amount and/or level of physical activity has been recorded. The removable component may include electrical contacts 2230 to communicate with the wrist strap 2210.

The removable component 2320 is depicted in FIG. 23 as being inserted into a base station 2350. The base station 2350 may serve to retrieve information from the removable component 2320 and transmit the information to a second device, such as the video game console as described above. The base station 2350 may also include a Universal Serial Bus adapter or other connector or coupling device so that the removable component 2320 may be coupled to a computer such as, for example, a personal computer. Information from the removable component 2320 may be transmitted to the personal computer if a user wishes to examine the precise levels of physical activity recorded by the removable component 2320 or if a user wishes to record all physical activity over time that has been recorded by the removable component 2320. The removable component 2320 may also be used to enable certain applications on the personal computer such as, for example, computer games. The removable component 2320 may also enable particular features of a application such as, for example, points in a particular game, different levels in a game, special skills in a game, or online currency redeemable for goods or services.

FIG. 24 depicts the removable component 2320 being inserted into a toy car 2460 In this embodiment, the toy car 2460 functions based on the amount and/or level of physical activity recorded by the removable component 2320. The car 2460 may, for example, only function for a specific time based on the amount and/or level of physical activity recorded by the removable component 2320. The car 2460 may also make special features available to a user based on the amount and/or level of physical activity recorded by the removable component 2320 such as super speed or stunt driving.

In one embodiment, the removable component includes a transmitter such as a RFID transmitter that communicates with devices such as, for example, toys or computer games. The transmitter will send a signal to such devices when a predetermined level of physical activity has been recorded by the removable component and the devices may activate or function in specific ways based on the signals. This obviates the need to insert the removable component into a second device for the second device to function in a specific way based on the amount and/or level of physical activity detected or recorded by the removable component. The transmitter may send signals to a second devices for a predetermined time based on the amount and/or level of physical activity recorded by the removable component or may send signals only while the removable component is presently detecting physical activity. When equipped with a transmitter, the removable component needs not be removable but instead may communicate with the second devices via radio frequency, infrared, or some other communications method or protocol.

The removable component may also accumulate points for the amount of physical activity recorded and these points may be uploaded to a web site through a computer. The web site may provide a variety of bonuses based on the amount of points accumulated by a user.

In one embodiment, a coupon may include intelligent logic that detects not only physical activity, but also levels of physical activity and types of physical activity. The coupon will discern between activities such as running, walking, and jumping jacks and record the level of a user's participation in each such activity. The coupon may require a user to participate in a predetermined level of a plurality of activities before the coupon is redeemable. The coupon may also include a plurality of indicators or displays each corresponding to one of a plurality of physical activities to alert the user when a predetermined threshold has been reached for each of the plurality of physical activities.

In an embodiment wherein a coupon detects a plurality of types of physical activity, the coupon may include a removable component which records the different types and levels of physical activity detected by the coupon. The removable component may then interact with a device such as, for example, a toy which will react to the amount and the types of physical activity recorded in the removable component by providing bonuses or special features based on the level and the type of physical activity the user has achieved. For example, the device may be a toy robot which includes a space for insertion of the removable component. If the removable component has recorded a predetermined threshold of jumping jacks, the toy robot may talk. If the removable component has recorded a predetermined threshold of running, the toy robot may walk. In this way, a device such as a toy will respond to the various physical activities achieved by a user. As described above, the removable coupon need not be removable.

Thus, while there have been shown, described, and pointed out fundamental novel features of the application as applied to a preferred embodiment thereof, it will be understood that various omissions, substitutions, and changes in the form and details of the devices illustrated, and in their operation, may be made by those skilled in the art without departing from the spirit and scope of the application. For example, it is expressly intended that all combinations of those elements and/or steps that perform substantially the same function, in substantially the same way, to achieve substantially the same results be within the score of the application. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book, or any other reference cited herein is each incorporated by reference in their entirety.

While this invention has been described in terms of several embodiments, it will be appreciated that those skilled in the art upon reading the preceding specifications and studying the drawings will realize various alterations, additions, permutations and equivalents thereof. Therefore, it is intended that the present invention includes all such alterations, additions, permutations, and equivalents as fall within the true spirit and scope of the invention.

What is claimed is:

1. An apparatus, comprising:
a motion detection component including circuitry for detecting and recording movement of the motion detection component;
a display defined to provide a visual indication of an amount of movement recorded by the circuitry;
an electrical contact for communication of signals associated with the detected and recorded movement of the motion detection component, the electrical contact defined to communicate signals to a secondary device, the signals associated with one or more of the detected and recorded movement of the motion detection component and a status of the apparatus, the electrical contact defined to be enclosed by a cover, the electrical contact positioned at an end of the apparatus; and
a band formed to secure to a part of a human body, the band including the motion detection component, the display, and the electrical contact, the band comprising a flexible material, the band defined such that the band is in a form of a coil in a relaxed state, the band defined such that the band is deformable upon application of a force to the band to enable positioning of the band around the part of the human body, the band defined such that upon removal of the force the band returns to the relaxed state to secure to the of the human body, wherein said circuitry is housed in the band.

2. An apparatus as recited in claim 1, wherein the circuitry is defined to direct the display to visually indicate an amount of points based on the amount of movement recorded by the circuitry.

3. An apparatus as recited in claim 1, wherein the display is defined to show an alphanumeric message, wherein the alphanumeric message indicates the amount of movement recorded by the circuitry.

4. An apparatus as recited in claim 1, further comprising:
a second electrical contact defined to communicate signals associated with the detected and recorded movement of the motion detection component from the motion detection component to other circuitry located within the band.

5. An apparatus as recited in claim 1, wherein the display is a plurality of light emitting diodes.

6. An apparatus as recited in claim 1, wherein the electrical contact is configured to communicate via a USB (universal serial bus) connection to the secondary device to transmit data associated with the detected and recorded movement to one or more of a website and a computer executable application for examining and viewing of the movement which represents physical activity by a user who wears the apparatus.

7. An apparatus as recited in claim 1, wherein the secondary device is one or more of a game, a toy, a game controller, a computer interface device, a cell phone, a mobile data communication device, a microprocessor, and a computer.

8. An apparatus as recited in claim 1, wherein the motion detection component is removable from the band.

9. An apparatus, comprising:
a motion detection component including circuitry for detecting and recording movement of the motion detection component;
a display defined to provide a visual indication of an amount of movement recorded by the circuitry;
a transmitter connected in electrical communication with the circuitry within the motion detection component, the transmitter configured to communicate recorded movement data to a secondary device;
a band formed to secure to a part of a human body, the band including the motion detection component, the display, and the transmitter, the band comprising a flexible material, the band defined such that the band is in a form of a coil in a relaxed state, the band defined such that the band is deformable upon application of a force to the band to enable positioning of the band around the part of the human body, the band defined such that upon removal of the force the band returns to the relaxed state to secure to the part of the human body, wherein said circuitry is housed in the band; and
a cover defined to attach to the band and detach from the band.

10. An apparatus as recited in claim 9, wherein the secondary device is a computer.

11. An apparatus as recited in claim 9, wherein the transmitter is configured to generate and transmit radio frequency signals in accordance with a communication protocol to communicate recorded movement data to the secondary device.

12. An apparatus as recited in claim 9, wherein the secondary device is one or more of a game, a toy, a game controller, a computer interface device, a cell phone, a mobile data communication device, a microprocessor, and a computer.

13. An apparatus, comprising:
a motion detection component including circuitry for detecting movement of the apparatus;
a movement threshold detection circuit defined to inject electrical charge into a capacitor in accordance with movement of the apparatus, the movement threshold detection circuit defined to transmit a triggering signal to power on the circuitry of the motion detection component when electrical charge in the capacitor reaches a preset threshold voltage level;
activity discernment logic defined to determine and record an amount of activity associated with the movement of the apparatus as detected by the motion detection component;
a notification component defined to signal when an amount of recorded activity has exceeded a predetermined amount of activity;
a band formed to secure to a part of a human body, the band including the motion detection component, the movement threshold detection circuit, the activity discernment logic, and the notification component.

14. An apparatus as recited in claim 13, wherein the notification component is defined to display an alphanumeric message indicating the amount of recorded activity.

15. An apparatus as recited in claim 13, wherein the activity discernment logic is defined to translate the amount of recorded activity into an amount of points, and wherein the notification component is defined to display the amount of points.

16. An apparatus as recited in claim 13, wherein the activity discernment logic is defined to determine a type of physical activity associated with the recorded activity and record an amount of the type of physical activity.

17. An apparatus as recited in claim 16, wherein the notification component is defined to indicate the recorded amount of the type of physical activity.

18. An apparatus as recited in claim 16, wherein the activity discernment logic is defined to determine multiple types of physical activity and separately record an amount of each of the multiple types of physical activity associated with the recorded activity.

19. An apparatus as recited in claim 18, wherein the notification component is defined to separately indicate the recorded amount of each of the multiple types of physical activity.

20. A system, comprising:
a band defined to be worn by a person, the band comprising a flexible material, the band defined such that the band is in a form of a coil in a relaxed state, the band defined such that the band is deformable upon application of a force to the band to enable positioning of the band around a part of the person, the band defined such that upon removal of the force the band returns to the relaxed state to secure to the part of the person; and
a physical activity tracking device positioned within the band, the physical activity tracking device including a motion detection component having circuitry for detecting and recording movement of the physical activity tracking device,
the physical activity tracking device including a notification component defined to indicate an amount of recorded movement of the physical activity tracking device, and
the physical activity tracking device including communication circuitry for communicating data associated with the amount of recorded movement of the physical activity tracking device to a secondary electronic device.

21. A system as recited in claim 20, wherein the physical activity tracking device includes an electrical contact for connecting the physical activity tracking device to the secondary electronic device.

22. A system as recited in claim 21, further comprising:
a coupling device defined to electrically connect the electrical contact to the secondary electronic device.

23. A system as recited in claim 22, wherein the coupling device is defined to connect to a Universal Serial Bus (USB) connector of the secondary electronic device.

24. A system as recited in claim 21, wherein the electrical contact is defined to electrically connect the communication circuitry to the secondary electronic device.

25. A system as recited in claim 20, wherein the physical activity tracking device includes a transmitter connected in electrical communication with the communication circuitry, the transmitter configured to wirelessly communicate data associated with the amount of recorded movement of the physical activity tracking device to the secondary electronic device.

26. A system as recited in claim 25, wherein the transmitter is configured to generate and transmit radio frequency signals in accordance with a communication protocol.

27. A system as recited in claim 20, wherein the secondary device is a computer.

28. A system as recited in claim 20, wherein the secondary device is one or more of a game, a toy, a game controller, a computer interface device, a cell phone, a mobile data communication device, a microprocessor, and a computer.

29. A system as recited in claim 20, wherein the physical activity tracking device is removable from the band.

30. A system as recited in claim 20, wherein the physical activity tracking device includes a computer processor and a computer memory, the computer memory having stored therein program instructions for a game defined to monitor physical activity of the person and provide feedback information to the person through the notification component based on the monitored physical activity of the person, the computer processor defined to execute the program instructions.

* * * * *